United States Patent
Rezania et al.

(10) Patent No.: US 10,421,948 B2
(45) Date of Patent: *Sep. 24, 2019

(54) METHODS FOR MAKING PANCREATIC ENDOCRINE CELLS

(71) Applicant: Janssen Biotech, Inc., Horsham, PA (US)

(72) Inventors: Alireza Rezania, Raritan, NJ (US); Benjamin Fryer, Horsham, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,594

(22) Filed: Aug. 22, 2017

(65) Prior Publication Data

US 2017/0355963 A1  Dec. 14, 2017

Related U.S. Application Data

(62) Division of application No. 14/963,436, filed on Dec. 9, 2015, now Pat. No. 9,752,126, which is a division of application No. 12/604,457, filed on Oct. 23, 2009, now Pat. No. 9,234,178.

(60) Provisional application No. 61/110,287, filed on Oct. 31, 2008.

(51) Int. Cl.
C12N 5/071 (2010.01)

(52) U.S. Cl.
CPC ...... *C12N 5/0676* (2013.01); *C12N 2501/115* (2013.01); *C12N 2501/117* (2013.01); *C12N 2501/155* (2013.01); *C12N 2501/16* (2013.01); *C12N 2501/39* (2013.01); *C12N 2501/405* (2013.01); *C12N 2501/41* (2013.01); *C12N 2501/70* (2013.01); *C12N 2501/998* (2013.01); *C12N 2506/02* (2013.01)

(58) Field of Classification Search
None
See application file for complete search history.

(56) References Cited

U.S. PATENT DOCUMENTS

| | | |
|---|---|---|
| 7,585,672 B2 | 9/2009 | Odorico et al. |
| 8,859,286 B2 | 10/2014 | Agulnik |
| 2003/0138948 A1 | 7/2003 | Fisk et al. |
| 2004/0121460 A1 | 7/2004 | Lumelsky et al. |
| 2005/0054102 A1 | 3/2005 | Wobus et al. |
| 2005/0260749 A1 | 11/2005 | Odorico et al. |
| 2005/0266554 A1 | 12/2005 | D'Amour |
| 2007/0259421 A1 | 11/2007 | D'Amour et al. |
| 2007/0259423 A1 | 11/2007 | Odorico et al. |
| 2008/0267926 A1 | 10/2008 | Martinson et al. |
| 2011/0281355 A1 | 11/2011 | Xu |
| 2012/0052576 A1 | 3/2012 | Rezania |
| 2013/0189777 A1 | 7/2013 | Rezania |

FOREIGN PATENT DOCUMENTS

| | | |
|---|---|---|
| JP | 2012/507292 | 3/2012 |
| WO | WO 2003/029445 | 4/2003 |
| WO | WO 2003/050249 | 6/2003 |
| WO | WO 2009/012428 | 1/2009 |
| WO | WO 2010/051223 | 5/2010 |
| WO | WO 2011/079017 | 6/2011 |
| WO | WO 2011/081222 | 7/2011 |
| WO | WO 2011/160066 | 12/2011 |
| WO | WO 2012/030540 | 3/2012 |

OTHER PUBLICATIONS

Jorda et al entitled "How Selective are Pharmacological Inhibitors of Cell-Cycle-Regulating Cyclin-Dependent Kinases?" (J. Med. Chem.; pp. A-P; published Sep. 20, 2018) (Year: 2018).*

Agulnick et al., "Insulin-producing endocrine cells differentiated in vitro from human embryonic stem cells function in macroencapsulation devices in vivo," *Stem Cells Transl Med* 4: 1214-1222 (e-pub Aug. 24, 2015).

Bose et al., "Human embryonic stem cell differentiation into insulin secreting β-cells for diabetes," *Cell Biology Intl.* 36(11): 1013-1020 (2012).

Cai et al., "Prospectively isolated NGN3-expressing progenitors from human embryonic stem cells give rise to pancreatic endocrine cells," *Stem Cells Translational Medicine* 3(4): 489-499 (e-pub Feb. 3, 2014).

D'Amour et al., "Production of pancreatic hormone—expressing endocrine cells from human embryonic stem cells," *Nature Biotechnology* 24(11): 1392-1401 (e-pub Oct. 19, 2006).

Fryer et al., "Generating β-cells in vitro: progress towards a holy grail," *Curr Opin Endocrinol Diabetes Obes* 20(2): 112-117 (Apr. 2013).

Jiang et al., "Generation of insulin-producing islet-like clusters from human embryonic stem cells," *Stem Cells* 25: 1940-1953 (2007).

Kroon et al., "Pancreatic endoderm derived from human embryonic stem cells generates glucose-responsive insulin-secreting cells in vivo," *Nature Biotechnology* 26(4): 443-452 (e-pub Feb. 20, 2008).

Pagliuca and Melton, "How to make a functional β-cell," *Development* 140(2): 2472-2483 (2013).

Wei et al., "Cdk5-dependent regulation of glucose-stimulated insulin secretion," *Nature Medicine* 11(10): 1104-1108 (e-pub Sep. 11, 2005).

(Continued)

*Primary Examiner* — Catherine S Hibbert

(74) *Attorney, Agent, or Firm* — Klarquist Sparkman, LLP

(57) ABSTRACT

The present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

13 Claims, 15 Drawing Sheets

(56) References Cited

OTHER PUBLICATIONS

Zhang et al., "Highly efficient differentiation of human ES cells and iPS cells into mature pancreatic insulin-producing cells," *Cell Research* 19: 429-438 (e-pub Mar. 3, 2009).

Zhang et al., "MafA ss a key regulator of glucose-stimulated insulin secretion," *Molecular and Cellular Biology* 25(12): 4969-4976 (Jun. 2005).

Zhao et al., "The islet β cell-enriched MafA activator is a key regulator of insulin gene transcription," *Journal of Biological Chemistry* 280(12): 11887-11894 (Mar. 25, 2005).

* cited by examiner

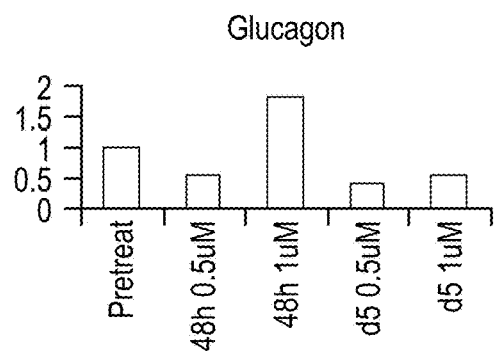
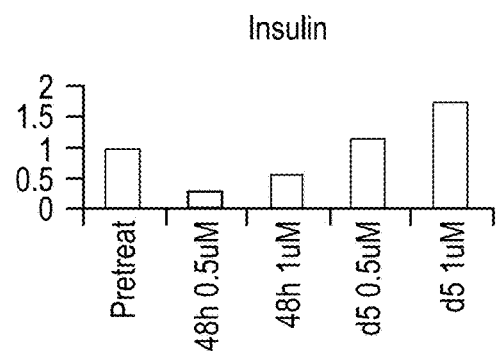
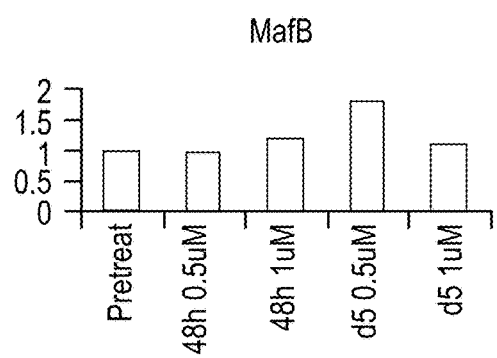
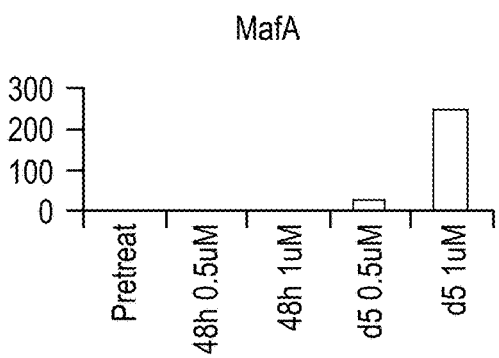
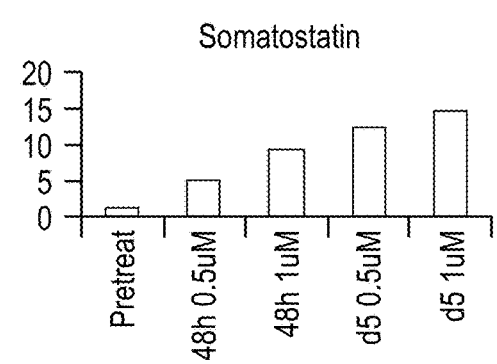
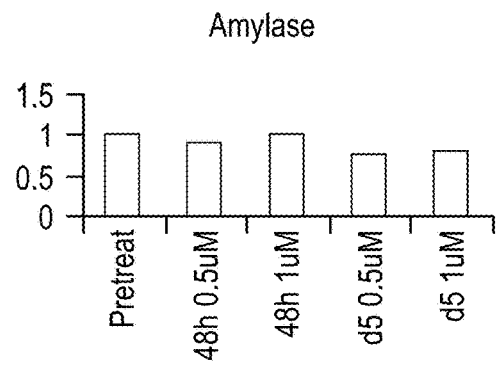

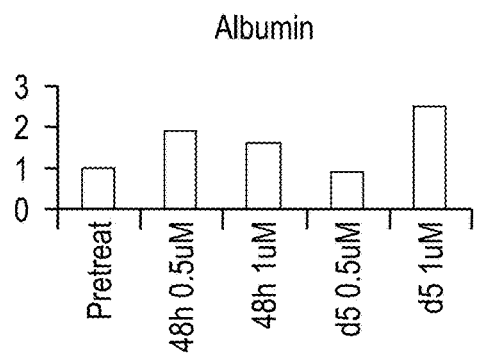
FIG. 3R — Albumin
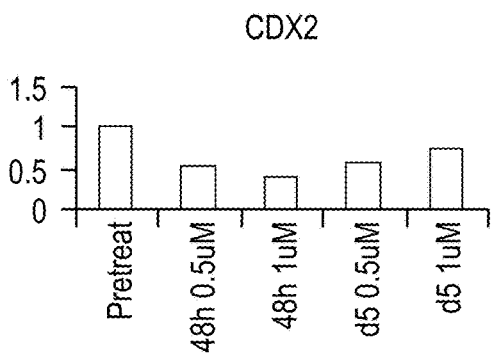
FIG. 3S — CDX2
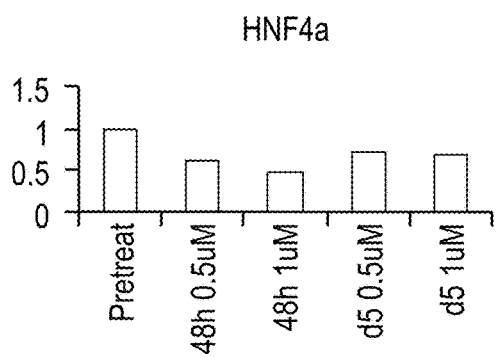
FIG. 3T — HNF4a
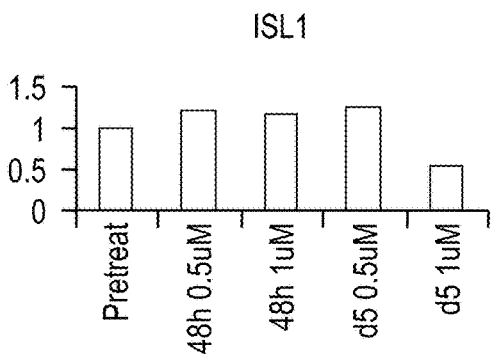
FIG. 3U — ISL1
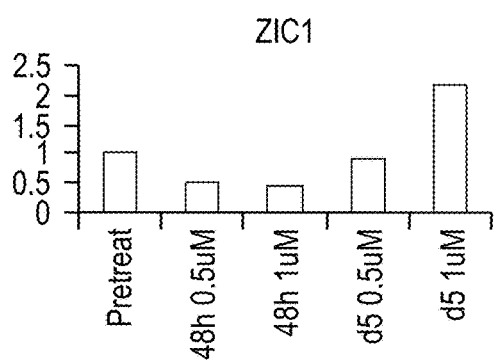
FIG. 3V — ZIC1
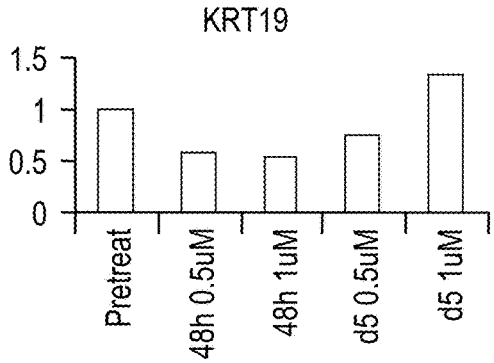
FIG. 3W — KRT19

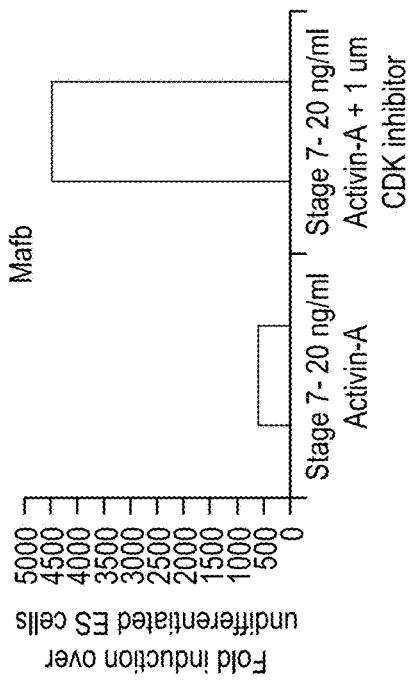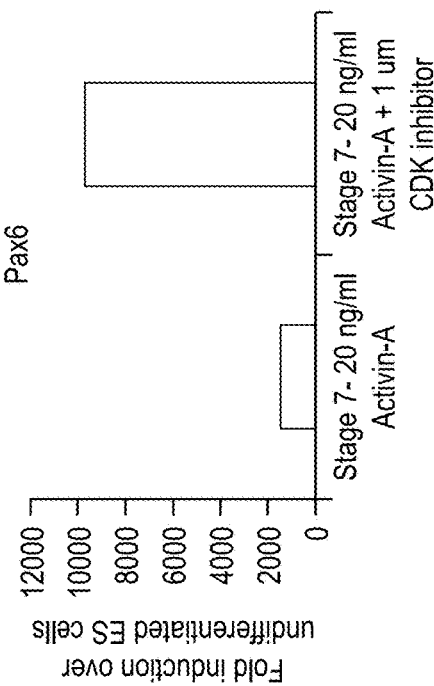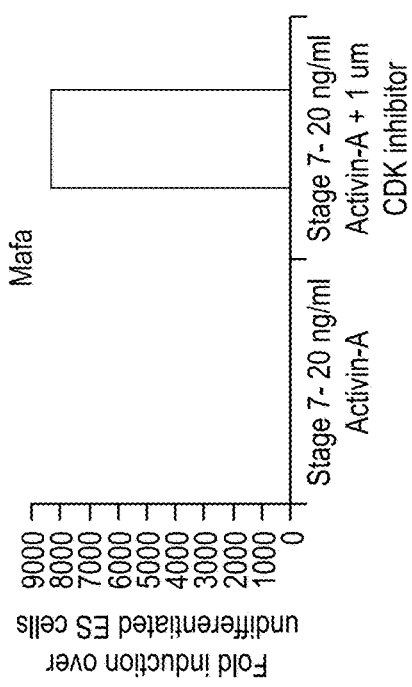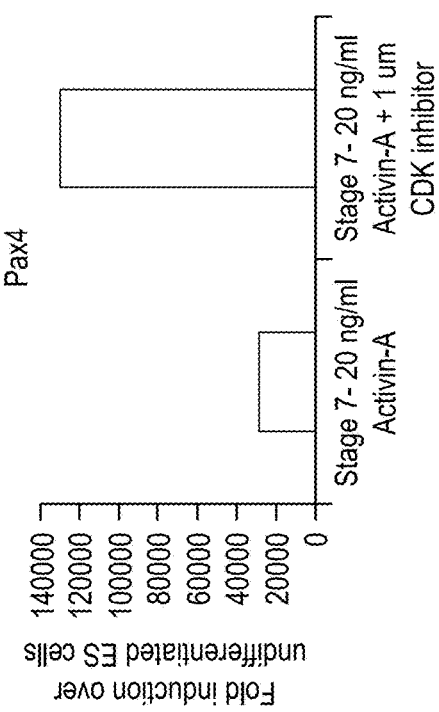

FIG. 4I
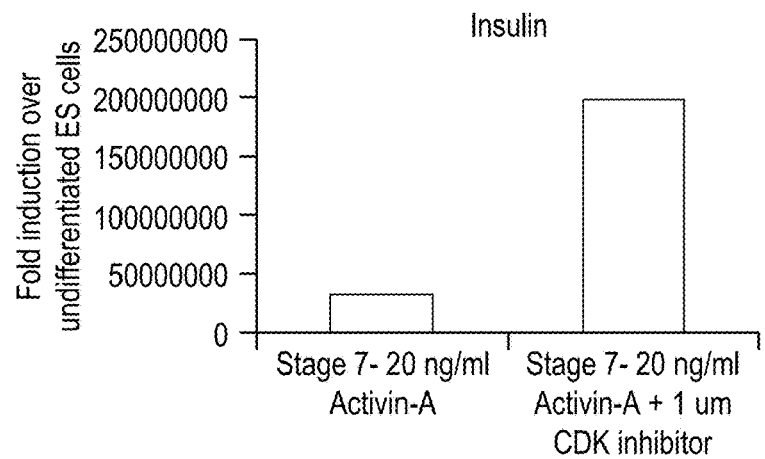
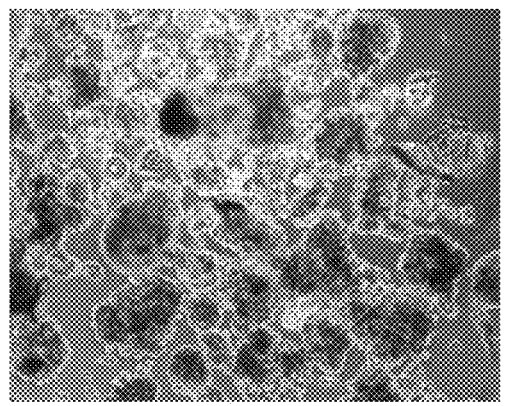
FIG. 5A
Control
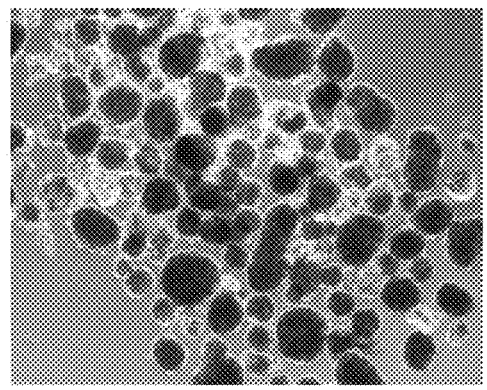
FIG. 5B
+ CDK inhibitor

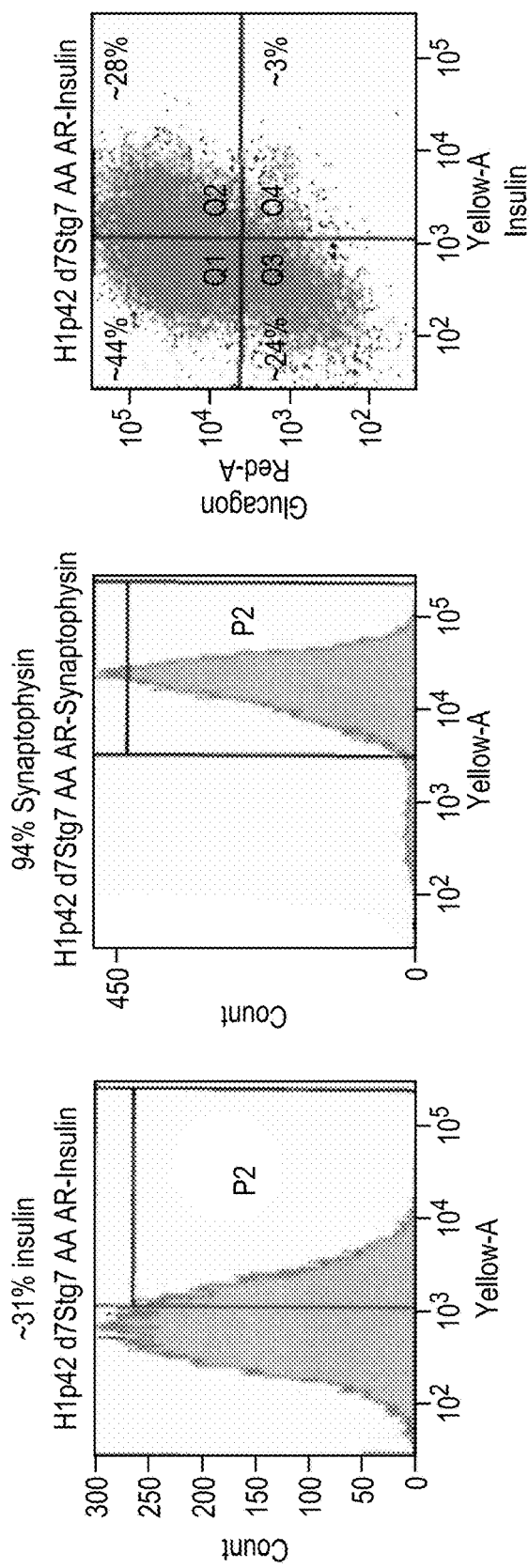

Glucagon

MAFA

Insulin

Somatostatin

METHODS FOR MAKING PANCREATIC ENDOCRINE CELLS

CROSS-REFERENCE TO RELATED APPLICATIONS

This application is a divisional of U.S. application Ser. No. 14/963,436, filed Dec. 9, 2015, which claims priority to U.S. application Ser. No. 12/604,457 filed Oct. 23, 2009 (now U.S. Pat. No. 9,234,178, issued Jan. 12, 2016), which claims priority to provisional Application No. 61/110,287, filed Oct. 31, 2008. The complete disclosures of the aforementioned related patent applications are hereby incorporated herein by reference for all purposes.

FIELD OF THE INVENTION

The present invention provides methods to promote the differentiation of pluripotent stem cells. In particular, the present invention provides a method to increase the expression of MAFA in cells expressing markers characteristic of the pancreatic endocrine lineage.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGF-β2 reproducibly yielded a higher proportion of Pdx1 positive cells (Genes Cells. 2005 June; 10(6): 503-16.).

Gordon et al. demonstrated the induction of brachyury$^+$/HNF-3beta$^+$ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology-24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930).

Cyclins have been implicated in beta cell function. For example, Lilja et al report that Cdk5 is present in the insulin-secreting pancreatic β-cell (J. Biol. Chem., Vol. 276, Issue 36, 34199-34205, Sep. 7, 2001). Lilja et al states "Cdk5 is present in β-cells and acts as a positive regulator of insulin exocytosis."

In another example, Marzo et al states "Cdk4 knockin mice have significantly increased beta cell mass and are physiologically functional, indicating that Cdk4 is a potential target for pancreatic beta cell mass regeneration in Type 1 diabetes" (Diabetalogia, Vol. 47, Number 4, 686-694, Apr. 1, 2004.)

In another example, Ubeda et al report that inhibition of cyclin-dependent kinase 5 activity protects pancreatic beta cells from glucotoxicity (J. Biol. Chem., Vol. 281, Issue 39, 28858-28864, Sep. 29, 2006).

In another example, Wei et al report Cdk5-dependent regulation of glucose-stimulated insulin secretion (Nature Medicine 11, 1104-1108 (1 Oct. 2005.)

In another example, Vanderford et al state "MafA is a basic leucine zipper transcription factor expressed within the beta cells of the pancreas and is required to maintain normal glucose homeostasis as it is involved in various aspects of beta cell biology. MafA protein levels are known to increase in response to high glucose through mechanisms that have yet to be fully characterized. We investigated whether discrete intracellular signaling events control mafA expression. We found that the general kinase inhibitor staurosporine induces mafA expression without altering the stability of the protein. Inhibition of the MAP-kinase JNK mimics the effects of staurosporine on the expression of mafA. Calmodulin kinase and calcium signaling are also important in stimulating mafA expression by high glucose. However, staurosporine, JNK, and calmodulin kinase have different effects on the induction of insulin expression. This data reveals that MafA levels are tightly controlled by the coordinated action of multiple kinase pathways." (Archives of Biochemistry and Biophysics (2008), doi: 10.1016/j.abb.2008.10.001).

Therefore, there still remains a significant need to develop methods for differentiating pluripotent stem cells into pancreatic endocrine cells, pancreatic hormone expressing cells, or pancreatic hormone secreting cells. The present invention provides methods to increase the expression of MAFA in cells expressing markers characteristic of the pancreatic endocrine lineage.

SUMMARY

In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

BRIEF DESCRIPTION OF THE DRAWINGS

FIGS. 4A-I show the effect of CDK inhibitor III treatment on the expression of markers characteristic of the pancreatic endocrine lineage in cells treated with Stage 7 of the differentiation protocol described in Example 4.

FIGS. 5A and 5B show the effect of CDK inhibitor III treatment on the dithazone staining of islet-like clusters.

FIGS. 6A-C show the expression of insulin, synaptophysin and glucagon in insulin-producing cells produced according to the methods described in Example 5. Expression of the proteins indicated was determined by FACS.

DETAILED DESCRIPTION

Figure 1A:
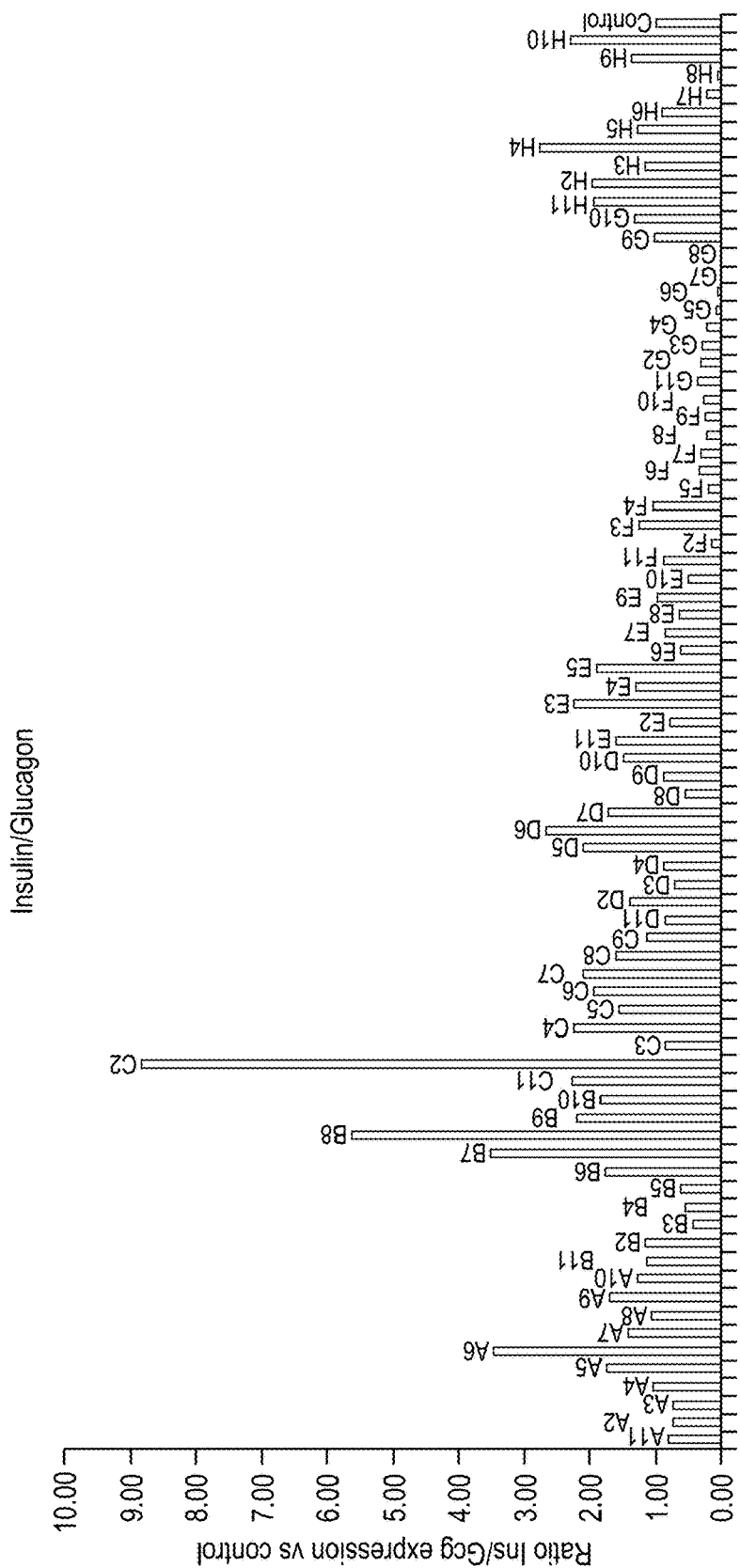
FIG. 1A shows the effect of compounds from the EMD Calbiochem kinase inhibitor library on the ratio of insulin to glucagon expression in cells expressing markers characteristic of the pancreatic endocrine lineage, as determined by real-time PCR. The alphanumeric label corresponds to the compound identity as shown in Table 1.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refers to cells with positive gene expression for the transcription factor PDX-1 and at least one of the following transcription factors: NGN3, NKX2.2, NKX6.1, NEUROD, ISL1, HNF3 beta, MAFA, PAX4, or PAX6. Cells expressing markers characteristic of the β cell lineage include β cells.

"Cells expressing markers characteristic of the definitive endoderm lineage", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF1 beta, PTF1 alpha, HNF-, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", as used herein, refers to cells expressing at least one of the following markers: NGN3, NEUROD, ISL1, PDX1, NKX6.1, PAX4, or PTF1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, or MIXL1.

"Extraembryonic endoderm", as used herein, refers to a population of cells expressing at least one of the following markers: SOX7, AFP, or SPARC.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell", as used herein, refers to a cell expressing at least one of the following markers: CD48, eomesodermin (EOMES), SOX17, DKK4, HNF3 beta, GSC, FGF17, or GATA6.

"Pancreatic endocrine cell", or "pancreatic hormone expressing cell", as used herein, refers to a cell capable of expressing at least one of the following hormones: insulin, glucagon, somatostatin, or pancreatic polypeptide.

"Pancreatic endoderm cell", as used herein, refers to a cell capable of expressing at least one of the following markers: NGN3, NEUROD, ISL1, PDX1, PAX4, or NKX2.2.

"Pancreatic hormone producing cell", as used herein, refers to a cell capable of producing at least one of the following hormones: insulin, glucagon, somatostatin, or pancreatic polypeptide.

"Pancreatic hormone secreting cell" as used herein, refers to a cell capable of secreting at least one of the following hormones: insulin, glucagon, somatostatin, and pancreatic polypeptide.

"Posterior foregut cell", as used herein, refers to a cell capable of secreting at least one of the following markers: PDX1, HNF1, PTF1 alpha, HNF6, HB9, or PROX1.

"Pre-primitive streak cell", as used herein, refers to a cell expressing at least one of the following markers: Nodal, or FGF8.

"Primitive gut tube cell", as used herein, refers to a cell capable of secreting at least one of the following markers: HNF1, or HNF4A.

"Primitive streak cell", as used herein, refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma # M7522; human recombinant basic fibroblast growth factor (bFGF), Gibco #13256-029.

Formation of Pancreatic Hormone Producing Cells from Pluripotent Stem Cells

In one embodiment, the present invention provides a method for producing pancreatic hormone producing cells from pluripotent stem cells, comprising the steps of:

a. Culturing pluripotent stem cells, b. Differentiating the pluripotent stem cells into cells expressing markers characteristic of the definitive endoderm lineage, c. Differentiating the cells expressing markers characteristic of the definitive endoderm lineage into cells expressing markers characteristic of the pancreatic endoderm lineage, and d. Differentiating the cells expressing markers characteristic of the pancreatic endoderm lineage into cells expressing markers characteristic of the pancreatic endocrine lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, Connexin43, Connexin45, OCT4, SOX2, NANOG, hTERT, UTF1, ZFP42, SSEA3, SSEA4, Tra1-60, or Tra1-81.

Markers characteristic of the definitive endoderm lineage are selected from the group consisting of SOX17, GATA4, HNF3 beta, GSC, CER1, NODAL, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, and PTF1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN3, NKX2.2, NKX6.1, NEUROD, ISL1, HNF3 beta, MAFA, PAX4, or PAX6. In one aspect of the present invention, a cell expressing markers characteristic of the β cell lineage is a β cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in US patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 60/990,529.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Differentiation of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, Connexin43, Connexin45, OCT4, SOX2, NANOG, hTERT, UTF1, ZFP42, SSEA3, SSEA4, Tra1-60, or Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529.

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, HLXB9, PTF1 alpha, PDX1, HNF6, or HNF1 beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage according to the methods disclosed in U.S. patent application Ser. No. 60/990,529.

In one aspect of the present invention, the present invention provides a method for increasing the expression of markers associated with the pancreatic endocrine lineage comprising treating cells expressing markers characteristic of the pancreatic endocrine lineage with medium comprising a sufficient amount of a TGF-(3 receptor agonist to cause an increase in expression of markers associated with the pancreatic endocrine lineage according to the methods disclosed in U.S. patent application Ser. No. 61/110,278.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN3, NEUROD, or ISL1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, PDX1, NKX2.2, NKX6.1, ISL1, PAX6, PAX4, NEUROD, HNF1 beta, HNF6, HNF3 beta, or MAFA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

In one aspect of the present invention, the efficiency of differentiation is determined by measuring the percentage of insulin positive cells in a given cell culture following treatment. In one embodiment, the methods of the present invention produce about 100% insulin positive cells in a given culture. In an alternate embodiment, the methods of the present invention produce about 90% insulin positive cells in a given culture. In an alternate embodiment, the methods of the present invention produce about 80% insulin positive cells in a given culture. In an alternate embodiment, the methods of the present invention produce about 70% insulin positive cells in a given culture. In an alternate embodiment, the methods of the present invention produce about 60% insulin positive cells in a given culture. In an alternate embodiment, the methods of the present invention produce about 50% insulin positive cells in a given culture. In an alternate embodiment, the methods of the present invention produce about 40% insulin positive cells in a given culture. In an alternate embodiment, the methods of the present invention produce about 30% insulin positive cells in a given culture. In an alternate embodiment, the methods of the present invention produce about 20% insulin positive cells in a given culture. In an alternate embodiment, the methods of the present invention produce about 10% insulin positive cells in a given culture. In an alternate embodiment, the methods of the present invention produce about 5% insulin positive cells in a given culture.

In one aspect of the present invention, the efficiency of differentiation is determined by measuring glucose-stimulated insulin secretion, as detected by measuring the amount of C-peptide released by the cells. In one embodiment, cells produced by the methods of the present invention produce about 1000 ng C-peptide/pg DNA. In an alternate embodiment, cells produced by the methods of the present invention produce about 900 ng C-peptide/pg DNA. In an alternate embodiment, cells produced by the methods of the present invention produce about 800 ng C-peptide/pg DNA. In an alternate embodiment, cells produced by the methods of the present invention produce about 700 ng C-peptide/pg DNA. In an alternate embodiment, cells produced by the methods of the present invention produce about 600 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 300 ng C-peptide/pg DNA. In an alternate embodiment, cells produced by the methods of the present invention produce about 200 ng C-peptide/pg DNA. In an alternate embodiment, cells produced by the methods of the present invention produce about 100 ng C-peptide/pg DNA. In an alternate embodiment, cells produced by the methods of the present invention produce about 90 ng C-peptide/pg DNA. In an alternate embodiment, cells produced by the methods of the present invention produce about 80 ng C-peptide/pg DNA. In an alternate embodiment, cells produced by the methods of the present invention produce about 70 ng C-peptide/pg DNA. In an alternate embodiment, cells produced by the methods of the present invention produce about 60 ng C-peptide/pg DNA. In an alternate embodiment, cells produced by the methods of the present invention produce about 50 ng C-peptide/pg DNA. In an alternate embodiment, cells produced by the methods of the present invention produce about 40 ng C-peptide/pg DNA. In an alternate embodiment, cells produced by the methods of the present invention produce about 30 ng C-peptide/pg DNA. In an alternate embodiment, cells produced by the methods of the present invention produce about 20 ng C-peptide/pg DNA. In an alternate embodiment, cells produced by the methods of the present invention produce about 10 ng C-peptide/pg DNA.

Increasing Expression of MAFA in Cells Expressing Markers Characteristic of the Pancreatic Endocrine Lineage In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependent kinase inhibitor to cause an increase in expression of MAFA.

The cyclin-dependent kinase inhibitor may inhibit cyclin-dependent kinase 1. Alternatively, the cyclin-dependent kinase inhibitor may inhibit cyclin-dependent kinase 2. Alternatively, the cyclin-dependent kinase inhibitor may inhibit cyclin-dependent kinase 4. Alternatively, the cyclin-dependent kinase inhibitor may inhibit cyclin-dependent kinase 5. Alternatively, the cyclin-dependent kinase inhibitor may inhibit cyclin-dependent kinase 9. Alternatively, the cyclin-dependent kinase inhibitor may inhibit multiple isoforms of cyclin-dependent kinase, in any combination thereof.

The cyclin-dependent kinase inhibitor may be a protein. Alternatively, the cyclin-dependent kinase inhibitor may be a peptide. Alternatively, the cyclin-dependent kinase inhibitor may be a small molecule. In one embodiment, the small molecule cyclin-dependent kinase inhibitor is selected from the group consisting of 7-n-Butyl-6-(4-hydroxyphenyl)[5H]pyrrolo[2,3-b]pyrazine, 9-Nitro-7,12-dihydroindolo[3,2-d][1]benzazepin-6(5H)-one, 3-(6-Oxo-9-nitro-5,6,7,12-tetrahydroindolo[3,2-d][1]benzazepin-2-yl)propionitrile, (2R)-2-((6-((3-Amino-5-chlorophenyl)amino)-9-(1-methylethyl)-9H-purin-2-yl)amino)-3-methyl-1-butanol, Arcyriaflavin A, [6-Benzylamino-2-(3-hydroxypropylamino)-9-isopropylpurine, Butyrolactone I, (Z)-1-(3-Ethyl-5-methoxy-2,3-dihydrobenzothiazol-2-ylidene)propan-2-one, 2-(3-Hydroxypropylamino)-6-(o-hydroxybenzylamino)-9-isopropylpurine, 1-(2,6-Dichlorophenyl)-1,5-dihydro-6-((4-(2-hydroxyethoxy)phenyl)methyl)-3-(1-methylethyl)-4H-pyrazolo[3,4-d]pyrimidin-4-one, Cdk/Cyclin Inhibitory Peptide III, 3-(2-Chloro-3-indolylmethylene)-1,3-dihydroindol-2-one, Ethyl-(6-hydroxy-4-phenylbenzo[4,5]furo[2,3-b])pyridine-3-carboxylate, RO-3306, N-(cis-2-Aminocyclohexyl)-N-(3-chlorophenyl)-9-ethyl-9H-purine-2,6-diamine, 6-Cyclohexylmethoxy-2-(4'-sulfamoylanilino)purine, 5-Amino-3-((4-(aminosulfonyl)phenyl)amino)-N-(2,6-difluorophenyl)-1H-1,2,4-triazole-1-carbothioamide, 3-Amino-1H-pyrazolo[3,4-b]quinoxaline, Cdk2 Inhibitor I, Cdk2 Inhibitor II, 2(bis-(Hydroxyethyl)amino)-6-(4-methoxybenzylamino)-9-isopropylpurine, 4-(6-Cyclohexylmethoxy-9H-purin-2-ylamino)-N,N-diethylbenzamide, N4-(6-Aminopyrimidin-4-yl)-sulfanilamide, (4-(2-Amino-4-methylthiazol-5-yl)pyrimidin-2-yl)-(3-nitrophenyl)amine, 2-Bromo-12,13-dihydro-5H-indolo[2,3-a]pyrrolo[3,4-c]carbazole-5,7(6H)-dione, 1,4-Dimethoxyacridine-9(10H)-thione, 5-(N-(4-Methylphenyl)amino)-2-methyl-4,7-dioxobenzothiazole, 4-(3,5-Diamino-1Hpyrazol-4-ylazo)-phenol, 2-(2-Hydroxyethylamino)-6-(3-chloroanilino)-9-isopropylpurine, Fascaplysin, Indirubin-3'-monoxime, Indirubin-3'-monoxime, 5-Iodo-, Indirubin-3'-monoxime-5-sulphonic Acid, Isogranulatimide, 2-(2-Hydroxyethylamino)-6-benzylamino-9-methylpurine, 6-(2-Hydroxybenzylamino)-2-((1R)-(hydroxymethyl)propyl)amino)-9-isopropylpurine, 5-Bromo-3-(2-(4-Fluorophenyl)-2-oxoethylidine)-1,3-dihydroindol-2-one, N6,N6-Dimethyladenine, 2-(1R-Isopropyl-2-hydroxyethylamino)-6-(3-chloroanilino)-9-isopropyl-purine, rapamycin, 2-(R)-(1-Ethyl-2-hydroxyethylamino)-6-benzylamino-9-isopropylpurine, Scytonemin, 3-[1-(3H-Imidazol-4-yl)-meth-(Z)-ylidene]-5-methoxy-1,3-dihydroindol-2-one, and 4-(3'-Hydroxyphenyl)amino-6,7-dimethoxyquinazoline.

In one embodiment, the cyclin-dependent kinase inhibitor is ethyl-(6-hydroxy-4-phenylbenzo[4,5]furo[2,3-b])pyridine-3-carboxylate. In one embodiment, ethyl-(6-hydroxy-4-phenylbenzo[4,5]furo[2,3-b])pyridine-3-carboxylate is added to cells expressing markers characteristic of the endocrine lineage at a concentration from about 0.1 µM to about 10 µM for about one to seven days.

In one embodiment, cells expressing markers characteristic of the endocrine lineage are treated with ethyl-(6-hydroxy-4-phenylbenzo[4,5]furo[2,3-b])pyridine-3-carboxylate for about one to about seven days.

The present invention is further illustrated, but not limited by, the following examples.

EXAMPLES

Example 1

Differentiation of Human Embryonic Stem Cells of the Cell Line H1 to Pancreatic Endocrine Cells in the Absence of Fetal Bovine Serum Cells of the human embryonic stem cells line H1 at passage 52 were cultured on MATRIGEL®-coated dishes (1:30 dilution) and exposed to the following differentiation protocol, in order to differentiate the cells to cells expressing markers characteristic of the pancreatic endocrine lineage.

a. RPMI medium supplemented with 2% BSA (Catalog#152401, MP Biomedical, Ohio), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, N.J.), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, Calif.) for two days (Stage 2), then c. DMEM/F12+1% B27 (Invitrogen, Calif.)+50 ng/ml FGF7+0.25 µM Cyclopamine-KAAD+2 µM Retinoic acid (RA) (Sigma, Mo.)+100 ng/ml of Noggin (R & D Systems, Minn.) for four days (Stage 3), then d. DMEM/F12+1% B27 (Invitrogen, Calif.)+100 ng/ml Noggin+1 µM DAPT (a gamma-secretase inhibitor) (Catalog#565784, Calbiochem, Calif.)+1 µM ALK5 inhibitor II (Catalog#616452, Calbiochem, Calif.)+100 ng/ml of Netrin-4 (R&D Systems, Minn.) for three days (Stage 4), then e. DMEM/F12+1% B27 (Invitrogen, Calif.)+1 µM ALK5 inhibitor II (Calbiochem, Calif.) for seven days (Stage 5).

Medium was changed daily. At each stage the cell number was calculated using a hemocytometer and RNA was collected for PCR analysis. All samples were collected in triplicate.

Example 2

Screening of the Effects of Compounds from the EMD Kinase Inhibitor Library II on Cells that have been Treated According to the Differentiation Protocol Outlined in Example 1

Cells of the human embryonic stem cell line H1 at passage 44 were seeded onto MATRIGEL™ coated 24-well dishes (1:30 dilution), and differentiated according to the methods described in Example 1 up to stage 5. Following this, the cells were treated for four days in DMEM/F12+1% B27 containing a compound from an EMD Calbiochem compound library (Catalog#539745, Calbiochem, San Diego, Calif.) at a final concentration of 1 µM. Wells containing vehicle were included as a control. Throughout the protocol media was changed daily. All samples were treated in duplicate. At the completion of this treatment RNA was collected for PCR analysis. Samples were analyzed by real-time PCR for expression of insulin, glucagon, MAFA, and Arx4. Results are expressed as a ratio insulin/glucagon (FIG. 1A), or MAFA versus ARX4 (FIG. 1B) of the treated samples relative to the untreated control, as measured by real-time PCR. The corresponding PubChem Compound ID# for each well # is listed in Table 1.

Figure 1B:
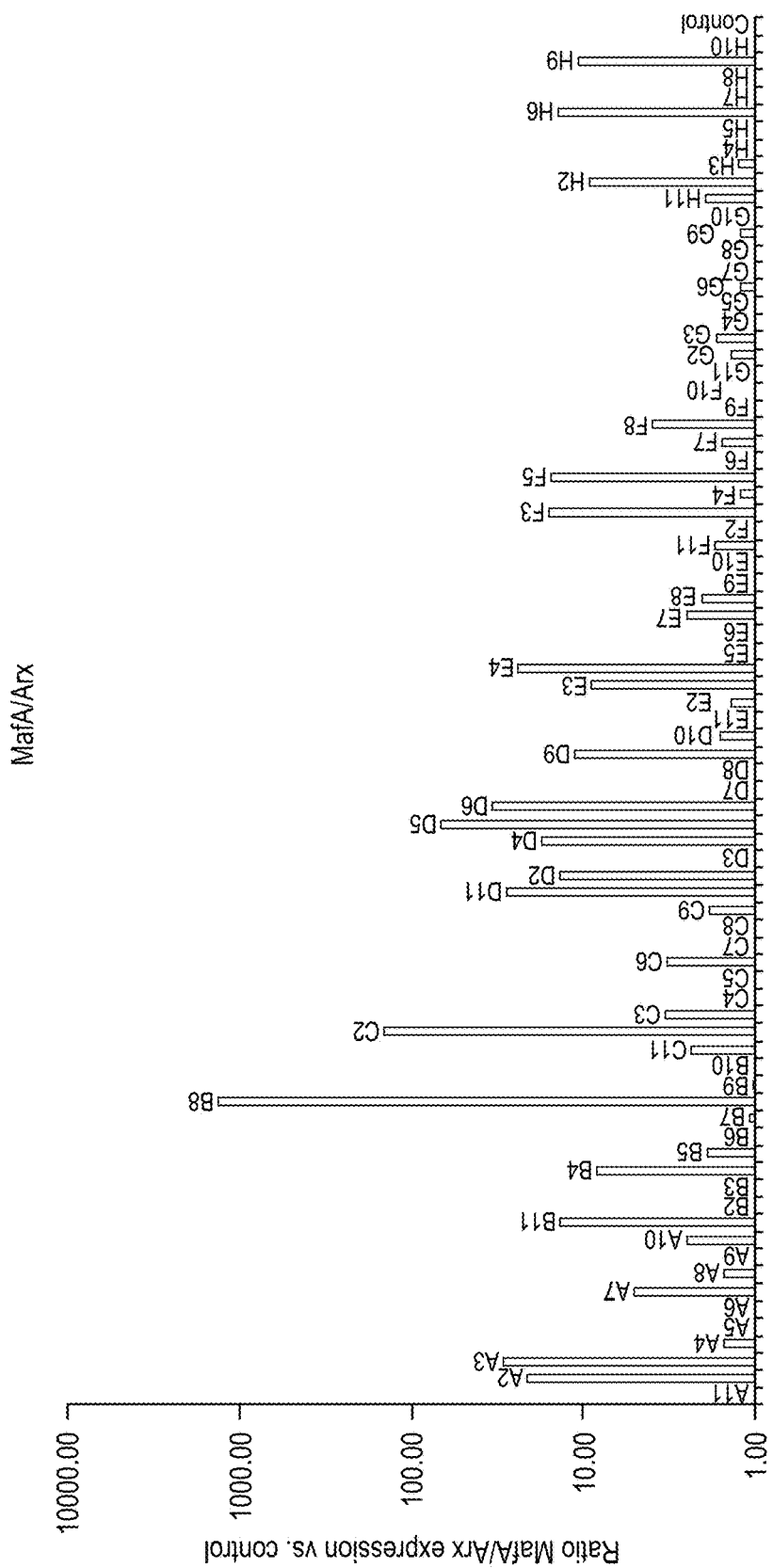
FIG. 1B shows the effect of compounds from the EMD Calbiochem kinase inhibitor library on the ratio of MAFA to ARX4 expression in cells expressing markers characteristic of the pancreatic endocrine lineage, as determined by real-time PCR. The alphanumeric label corresponds to the compound identity as shown in Table 1.

Treatment of cells expressing markers characteristic of the pancreatic endocrine lineage with compounds A6, B7, B8, or C2 at a 1 µM concentration resulted in an insulin/glucagon expression ratio of approximately 3.0 or higher (see FIG. 1A).

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound B8 showed a ratio of MAFA/ARX4 of approximately 1000. Treatment of cells expressing markers characteristic of the pancreatic endocrine lineage with compound C2 resulted in a MAFA/ARX4 ratio of approximately 100. (See FIG. 1B).

Example 3

The Effects of Cyclin-Dependent Kinase Inhibitor Treatment on Insulin and MAFA Expression in Cells that have been Treated According to the Differentiation Protocol Outlined in Example 1

Figure 2C:
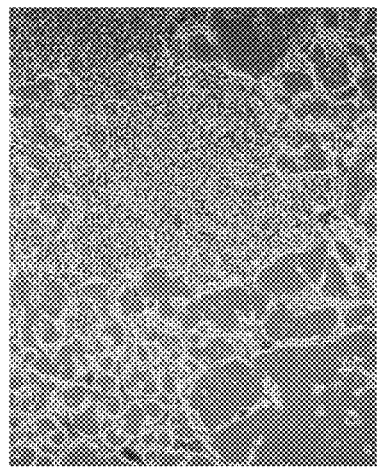
FIG. 2C shows a 4× micrograph of cells treated with 1 µM of the compound PubChemID#5330812 at day 4 of treatment.
Figure 2B:
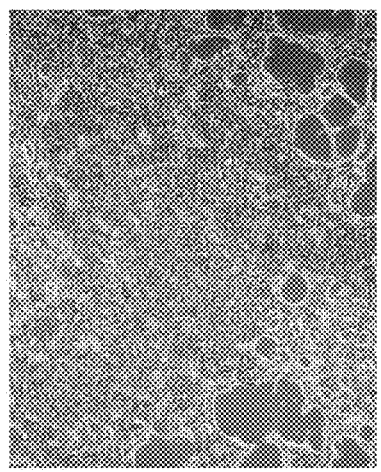
FIG. 2B shows a 4× micrograph of cells treated with 0.5 µM of the compound PubChemID#5330812 at day 4 of treatment.
Figure 2A:
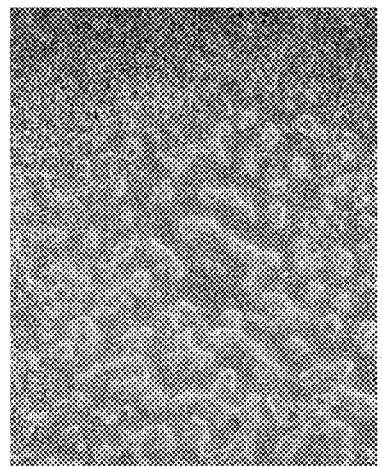
FIG. 2A shows a 4× micrograph of cells treated according to the methods described in Example 1, at day 4 of the stage 6 treatment.
Figure 2F:
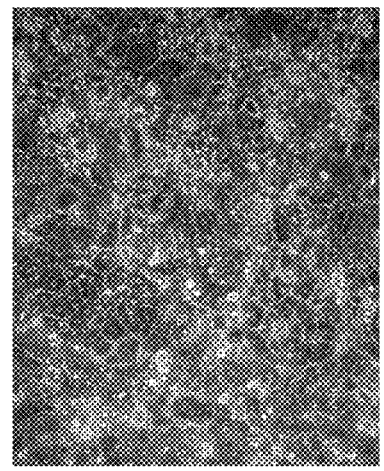
FIG. 2F shows a 20× micrograph of cells treated with 1 µM of the compound PubChemID#5330812 at day 6 of treatment.
Figure 2E:
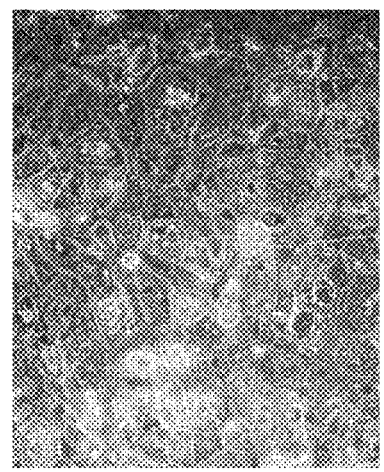
FIG. 2E shows a 20× micrograph of cells treated with 0.5 µM of the compound PubChemID#5330812 at day 6 of treatment.
Figure 2D:
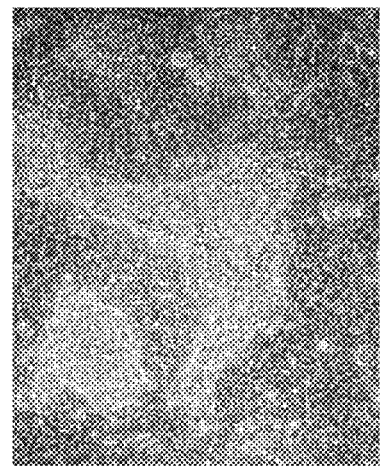
FIG. 2D shows a 20× micrograph of cells treated according to the methods described in Example 1, at day 6 of the stage 6 treatment.
Figure 3G:
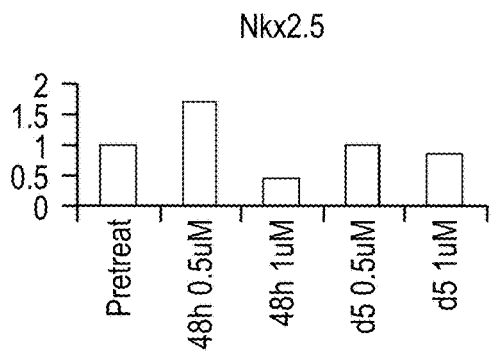
FIGS. 3A-W show the expression of the 23 genes indicated, in cells expressing markers characteristic of the pancreatic endocrine lineage following a five-day treatment of 0.5 µM (dark bars) or 1.0 µM (light bars) of the compound PubChem ID#5330812. Expression levels were determined at day 0, day 2 and day 5.

Several of the compounds that increased the ratio of insulin to glucagon expression, or MAFA to ARX4 expression in Example 2 were cyclin-dependent kinase inhibitors. One such compound was PubChem Compound ID#5330797 (5-Amino-3-((4-(aminosulfonyl)phenyl)amino)-N-(2,6-difluorophenyl)-1H-1,2,4-triazole-1-carbothioamide) (Catalogue #217714; Calbiochem, San Diego, Calif.). To confirm these observations, cells of the human embryonic stem cell line H1 at passage 42 were cultured in 10 cm$^2$ MATRIGEL®-coated dishes and treated according to the methods described in Example 1 up to stage 5. After stage 5, the cells were treated with DMEM/F12 containing 1% B27 containing 1 µM PubChem Compound ID#5330797 for six days. Medium was changed every other day. Samples of cells were taken for real-time PCR prior to treatment with the compound, and at days two and five of compound treatment Characteristic micrographs of the cells at day 4 or day 6 of compound treatment versus untreated controls are shown in FIGS. 2A-2F. Untreated cells are highly packed (FIGS. 2A and 2D) and it is difficult to distinguish individual cells. However, after treatment with 0.5 µM or 1 µM of PubChem Compound ID#5330797 for six days, individual nuclei became visible (FIGS. 2E and 2F) as compared to the untreated control (FIG. 2D), indicating that there was differentiation occurring in the cell population. This was also accompanied by some cell death, which can be seen by gaps in the layer of cells as shown in FIGS. 2B and 2C Treatment of cells with PubChem Compound ID#5330797 resulted in the increase in expression of insulin, glucagon, MAFA, MAFB and somatostatin, albeit to differing degrees. The relative induction of gene expression per treatment as compared to day 0 (pretreatment) cultures is shown in FIGS. 3A-3V. Cells expressing markers characteristic of the pancreatic endocrine lineage that were treated with 1 µM PubChem Compound ID#5330797 resulted in an approximately 1.5 fold increase in glucagon expression at 48 hrs of treatment. This expression declined to below pretreatment levels after 5 days of treatment. No increase in glucagon expression was observed with treatment of 0.5 µM PubChem Compound ID#5330797. (See FIG. 3A).

Cells expressing markers characteristic of the pancreatic endocrine lineage that were treated with 1 µM PubChem Compound ID#5330797 for five days resulted in an approximately 1.5 fold increase in insulin expression. (See FIG. 3B).

Cells expressing markers characteristic of the pancreatic endocrine lineage that were treated with 1 µM PubChem Compound ID#5330797 for five days resulted in an approximately 200 fold increase in MAFA expression. (See FIG. 3D).

Cells expressing markers characteristic of the pancreatic endocrine lineage that were treated with 0.5 µM PubChem Compound ID#5330797 for five days resulted in an approximately 1.5 fold increase in MAFB expression. (See FIG. 3C). A dose-dependent increase in the expression of somatostatin was observed (FIG. 3E)

Figure 3H:
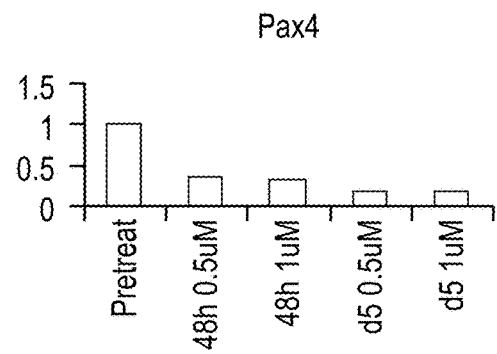
Figure 3I:
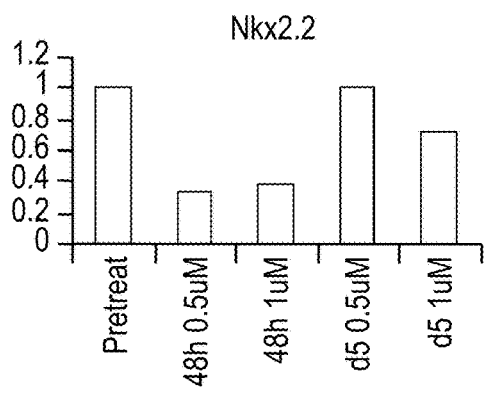
Figure 3J:
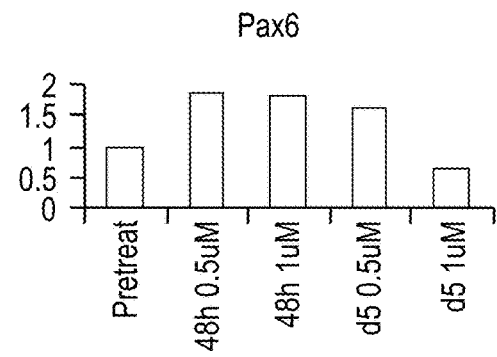
Figure 3K:
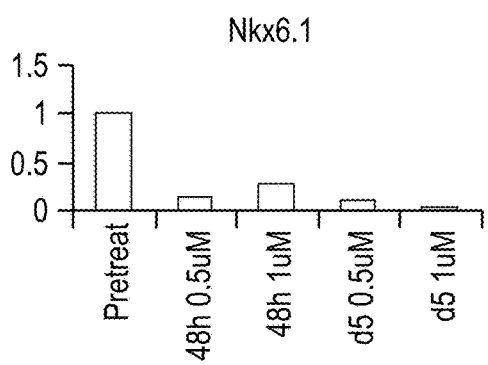
Figure 3L:
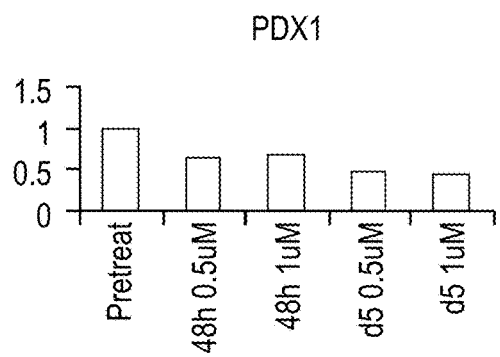
Figure 3M:
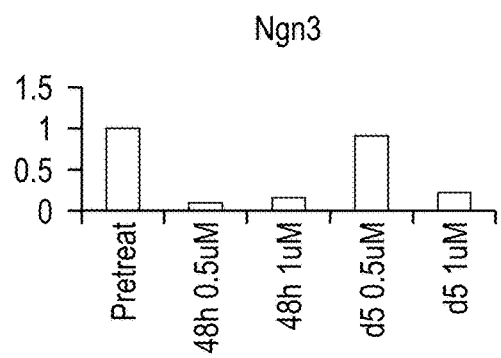
Figure 3N:
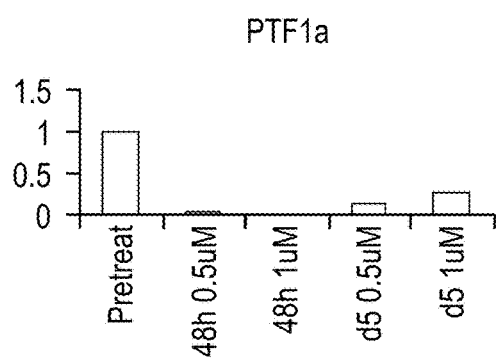
Figure 3O:
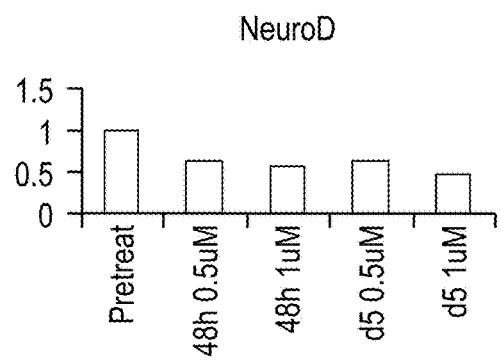
Figure 3P:
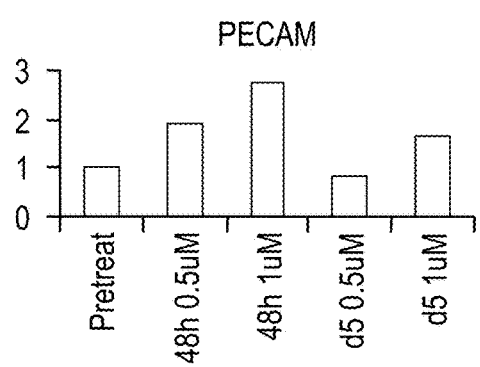
Figure 3Q:
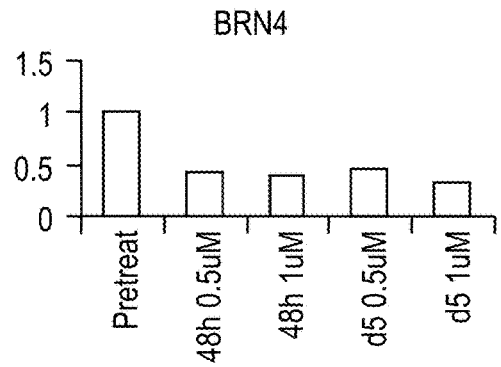
Figure 4E:
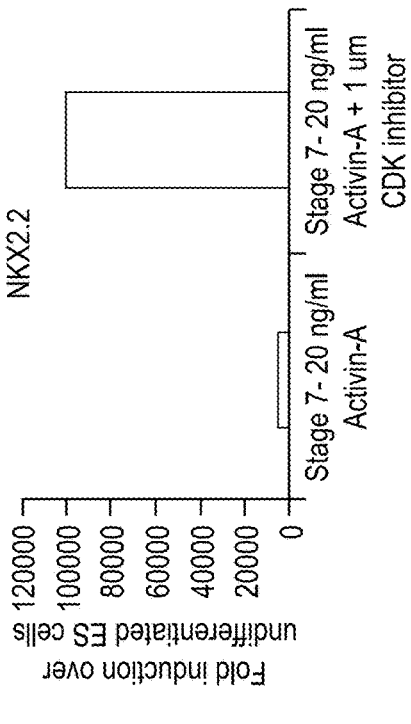
Figure 4F:
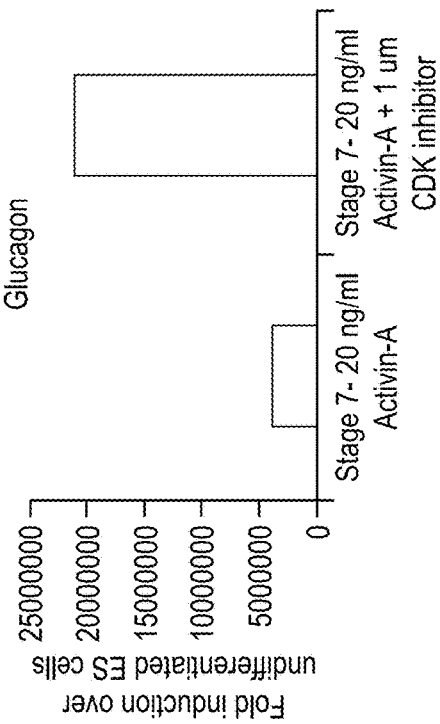
Figure 4G:
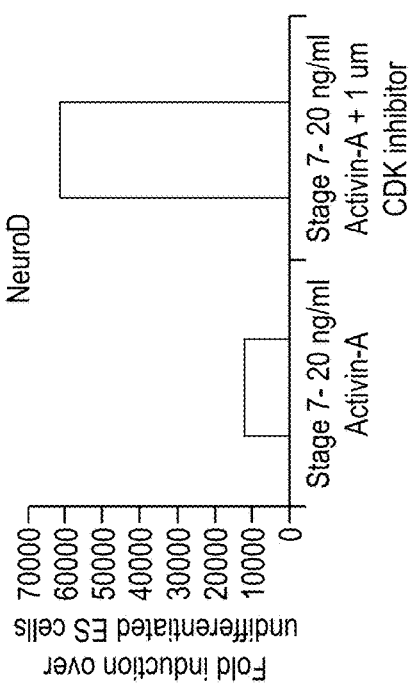
Figure 4H:
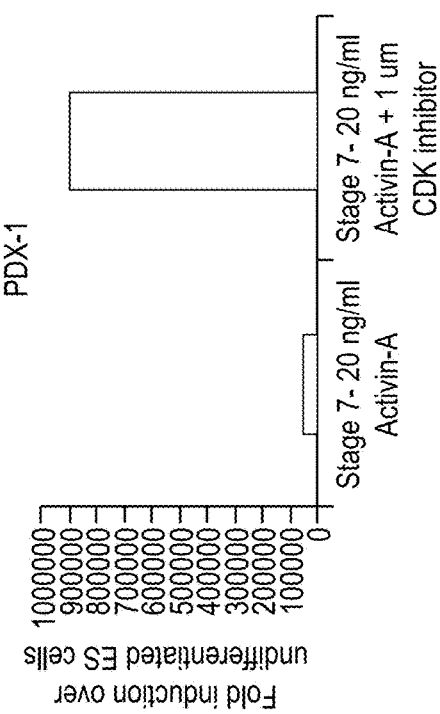

No change in the expression of amylase was observed in cells expressing markers characteristic of the pancreatic endocrine lineage that were treated with PubChem Compound ID#5330797 for five days. (See FIG. 3F). However, decreases in the level of expression of PAX4 (FIG. 3H), NKX6.1 (FIG. 3K), PDX1 (FIG. 3L), NEUROD (FIG. 3O), and BRN4 (FIG. 3Q) was observed.

Example 4

Cyclin-Dependent Kinase Inhibitor Treatment Increased the Expression of MAFA in Islet-Like Clusters Cells of the human embryonic stem cell line H1 at passage 52 were cultured on MATRIGEL® coated dishes (1:30 dilution) and differentiated according to the methods described in Example 1. An additional stage (Stage 6) was added, in order to further mature the cells expressing markers characteristic of the pancreatic endocrine lineage. Stage 6 in this example consisted of a seven day treatment in DMEM/F12+1% B27 (Invitrogen, Calif.). The medium was changed daily.

After stage 6, the cells were treated for 5 mins at room temperature with 1× accutase (Sigma, Mo.). The accutase was removed, and DMEM/12+1% B27 was added to the cells. The attached cells were removed using a cell scarper and gently resuspended and passed through a 40 µm cell strainer. The cells retained on the strainer were removed by rinsing in basal media and cultured in suspension on Ultra-Low culture plates (Catalogue#3471, Corning, Mass.). The cells were then treated as follows: The cells were cultured in DMEM/F12+1% B27, containing 20 ng/ml of activin A (AA), 1 µm of CDK inhibitor III (Catalog#217714, Calbiochem, Calif.) for 10 days (Stage 7). Cells treated with vehicle were included as controls. Samples were collected at days 7 through 10 for PCR analysis and dithizone staining. The cells cultured in suspension according to the methods outlined in this example assumed a morphology similar to pancreatic islet clusters. Treatment with CDK inhibitor III did not appear to affect the morphology of the islet like clusters FIGS. 4A-4I show the effect of CDK inhibitor III treatment on gene expression profile of the cell clusters. Treatment with of CDK inhibitor III increased the expression of markers associated with the pancreatic endocrine lineage and in particular increased the expression of the pro-insulin transcription factor, MAFA FIGS. 5A-5B show the effect of CDK inhibitor III on dithazone (DTZ) staining of clusters. Cell clusters treated with CDK inhibitor and stained with DTZ, showed a more reddish staining pattern as compared to clusters not treated with the CDK inhibitor III.

Example 5

FACS Analysis of Insulin Producing Cells Produced by the Methods of the Present Invention Cells of the human embryonic stem cell line H1 at passage 42 were cultured on MATRIGEL®-coated plates, and differentiated into insulin producing cells using the following protocol:

a. RPMI medium supplemented with 2% BSA (Catalog#152401, MP Biomedical, Ohio), and 100 ng/ml activin A (R&D Systems, Minn.) plus 20 ng/ml WNT-3a (Catalog#1324-WN-002, R&D Systems, Minn.) plus 8 ng/ml of bFGF (Catalog#100-18B, PeproTech, N.J.), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, Calif.) for two days (Stage 2), then c. DMEM/F12+1% B27 (Invitrogen, Calif.)+50 ng/ml FGF7+0.25 µM Cyclopamine-KAAD+2 µM Retinoic acid (RA) (Sigma, Mo.)+100 ng/ml of Noggin (R & D Systems, MN) for four days (Stage 3), then d. DMEM/F12+1% B27 (Invitrogen, Calif.)+100 ng/ml Noggin+1 µM DAPT (a gamma-secretase inhibitor) (Catalog#565784, Calbiochem, Calif.)+1 µM ALK5 inhibitor II (Catalog#616452, Calbiochem, Calif.)+100 ng/ml of Netrin-4 (R&D Systems, Minn.) for three days (Stage 4), then e. DMEM/F12+1% B27 (Invitrogen, Calif.)+1 µM ALK5 inhibitor II (Calbiochem, Calif.) for seven days (Stage 5), then f. DMEM/F12+1% B27 for seven days (Stage 6), then g. Treatment with Accutase for 5 minutes, followed by scraping to remove any remaining attached cells. The cell suspension was then passed through a 40 µm cell strainer. The cells retained on the strainer were removed by rinsing in basal media and cultured in suspension on Ultra-Low culture plates in DMEM-High Glucose (Catalogue#11995-073, Invitrogen, Calif.)+1% B27+20 ng/ml of activin A (AA) 1 µm of CDK inhibitor III (Catalog#217714, Calbiochem, Calif.) for 5 days (Stage 7).

Islet-like clusters were dispersed into single cells using TrypLE Express (Invitrogen, Carlsbad, Calif.) and washed in cold PBS. For fixation, the cells were resuspended in 200-300 µl Cytofix/Cytoperm Buffer (BD 554722, BD, Ca) and incubated for 30 min at 4° C. Cells were washed two times in 1 ml Perm/Wash Buffer Solution (BD 554723) and resuspended in 100 µl staining/blocking solution containing 2% normal goat serum in Perm/Wash buffer. For flow cytometric analysis, cells were stained with the following primary antibodies: Anti-Insulin (Rabbit mAb, Cell Signaling No. C27C9; 1:100 dilution); Anti-Glucagon (Mouse Mab, Sigma No. G2654, 1:100); Anti-Synaptophysin (Rabbit Polyclonal antibody, DakoCytomation No A0010, 1:50). Cells were incubated for 30 min at 4° C. followed by two washes in Perm/Wash buffer and a further 30 min incubation in appropriate secondary antibodies as follows: Goat anti-Rabbit Alexa 647 (Invitrogen No. A21246) or Goat anti-Mouse 647 (Invitrogen No. A21235); Goat anti-Rabbit R-PE (BioSource No. ALI4407). All secondary antibodies were used at a 1:200 dilution. Cells were washed at least once in Perm/Wash buffer and analyzed using BD FACSArray. At least 10,000 events were acquired for analysis. Controls included undifferentiated H1 cells and the β-TC (CRL-11506™ ATCC, VA) cell line.

Figure 7C:
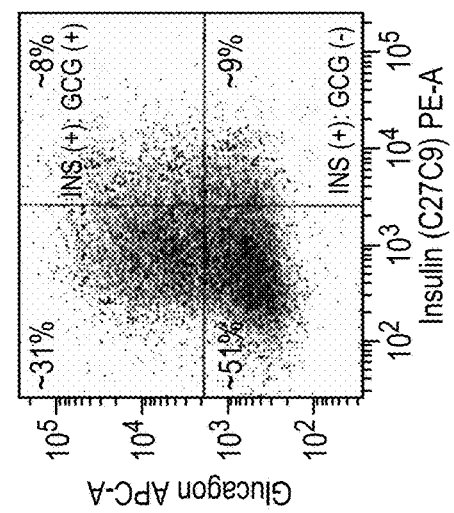
FIGS. 7A-C show the expression of insulin, synaptophysin and glucagon in insulin-producing cells produced according to the methods described in Example 5. Expression of the proteins indicated was determined by FACS.
Figure 7B:
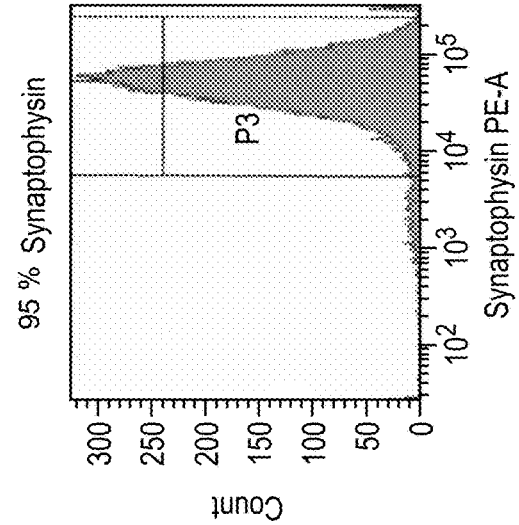
Figure 7A:
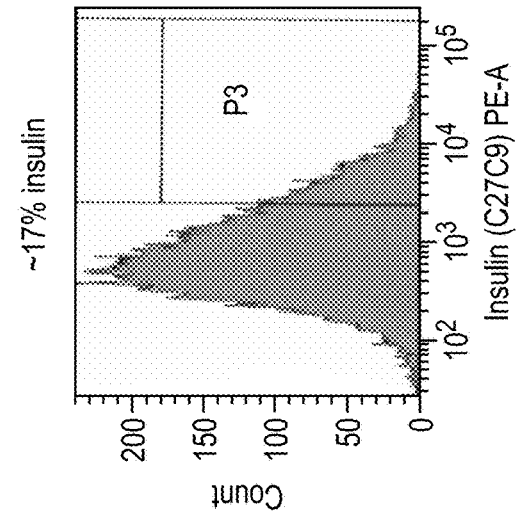

FIGS. 6A-6C show the percentage insulin positive, synapthophysin positive, and glucagon positive cells in cells following treatment with Stage 7, in medium containing vehicle. FIGS. 7A-7C show the percentage insulin positive, synapthophysin positive, and glucagon positive cells following treatment with Stage 7 in medium containing 1 µM CDK inhibitor III for 5 days. The number of single hormonal insulin positive cells increased from 3% to 8% following treatment with the CDK inhibitor. Additionally, the percentage of poly hormonal (insulin and glucagon positive) cells decreased following treatment with the CDK inhibitor.

Example 6

Kinetics of CDK Inhibitor-Induced MAFA Expression

Cells of the human embryonic stem cell line H1 at passage 42 were cultured on MATRIGEL®-coated plates, and differentiated into insulin producing cells using the following protocol:

a. RPMI medium supplemented with 2% BSA (Catalog#152401, MP Biomedical, Ohio), and 100 ng/ml activin A (R&D Systems, Minn.) plus 20 ng/ml WNT-3a (Catalog#1324-WN-002, R&D Systems, Minn.) plus 8 ng/ml of bFGF (Catalog#100-18B, PeproTech, N.J.), for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, Calif.) for two days (Stage 2), then c. DMEM/F12+1% B27 (Invitrogen, Calif.)+50 ng/ml FGF7+0.25 µM Cyclopamine-KAAD+2 µM Retinoic acid (RA) (Sigma, Mo.)+100 ng/ml of Noggin (R & D Systems, Minn.) for four days (Stage 3), then d. DMEM/F12+1% B27 (Invitrogen, Calif.)+100 ng/ml Noggin+1 µM DAPT (a gamma-secretase inhibitor) (Catalog#565784, Calbiochem, Calif.)+1 µM ALK5 inhibitor II (Catalog#616452, Calbiochem, Calif.)+100 ng/ml of Netrin-4 (R&D Systems, Minn.) for three days (Stage 4), then e. DMEM/F12+1% B27 (Invitrogen, Calif.)+1 µM ALK5 inhibitor II (Calbiochem, Calif.) for seven days (Stage 5), then f. DMEM/F12+1% B27 for seven days (Stage 6), then g. Treatment with Accutase for 5 minutes, followed by scraping to remove any remaining attached cells. The cell suspension was then passed through a 40 µm cell strainer. The cells retained on the strainer were removed by rinsing in basal media and cultured in suspension on Ultra-Low culture plates in DMEM-High Glucose (Catalogue#11995-073, Invitrogen, Calif.)+1% B27+20 ng/ml of activin A (AA) 2 µm of CDK inhibitor III (Catalog#217714, Calbiochem, Calif.) for 1-8 days (Stage 7).

Samples were collected for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.

Figure 8A:
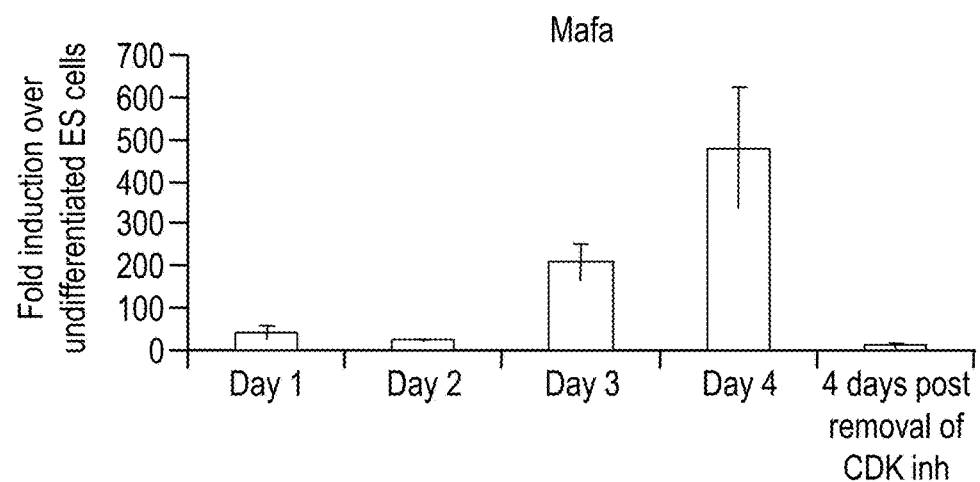
FIGS. 8A and 8B show the expression of MAFA and insulin, respectively, in insulin-producing cells, produced by the methods of the present invention. Samples of cells were taken for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.
Figure 8B:
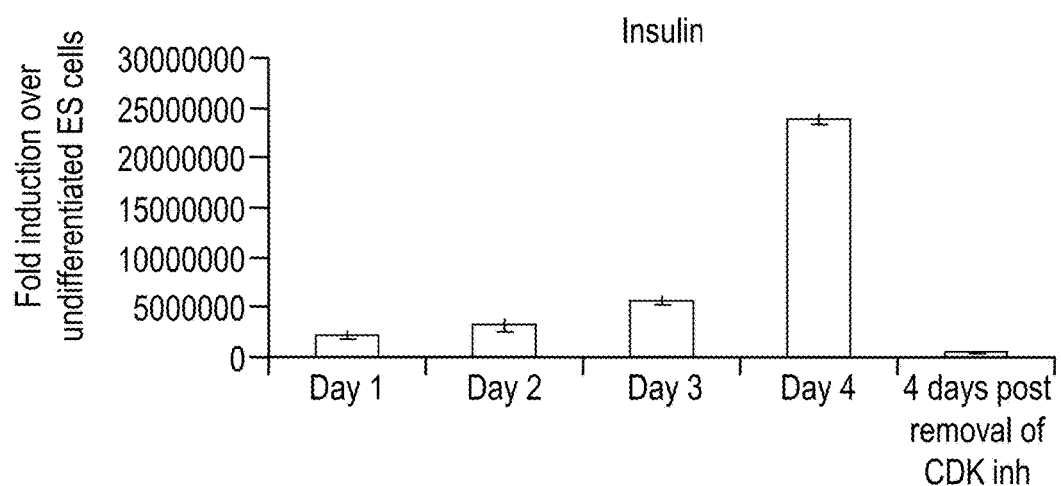

FIGS. 8A-8B show expression pattern of MAFA and insulin at various time points of stage 7. CDK inhibitor treatment resulted in significant increase in MAFA and insulin expression which increased as a function of time. However, removal of CDK inhibitor resulted in a significant drop to both MAFA and insulin expression, in samples obtained four days after removal of the compound.

Example 7

Screening of the Effects of Compounds from the BIOMOL™ Kinase Inhibitor Library on Cells that have been Treated According to the Differentiation Protocol Outlined in Example 1

Cells of the human embryonic stem cell line H1 at passage 51 were seeded onto MATRIGEL®-coated 24-well dishes (1:30 dilution), and differentiated according to the methods described in Example 1 up to stage 5. Following this, the cells were grown for one day in DMEM/F12+1% B27 and then treated for six days in DMEM/F12+1% B27 containing a compound from a BIOMOL™ compound library (Catalog#2832, BIOMOL, Plymouth Meeting, Pa.) at a final concentration of 4 µM. Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as a ratio insulin/glucagon (Table 2), or MAFA versus Arx4 (Table 2) of the treated samples relative to the untreated control, as measured by real-time PCR. The corresponding catalog#, CAS#, and compound name or ID number for each alpha numeric well# is listed in Table 3.

Treatment of cells expressing markers characteristic of the pancreatic endocrine lineage with compounds C8 or F1 at a 4 µM concentration resulted in an insulin/glucagon expression ratio of approximately 10.0 or higher. Cells treated with D9 had an insulin/glucagon expression ratio of approximately 1840.0 (Table 2)

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound B6 or F1 showed a ratio of MAFA/ARX4 of approximately greater than 10. Treatment of cells expressing markers characteristic of the pancreatic endocrine lineage with compound C8 resulted in a MAFA/ARX4 ratio of approximately 84, while cells treated with D9 had a MAFA/ARX4 ratio of approximately 212. (Table 2).

Example 8

The Effect of Cyclin-Dependent Kinase Inhibitors on Insulin and MAFA Expression in Cells Treated According to the Differentiation Protocol Outlined in Example 1

Cells of the human embryonic stem cell line H1 at passage 51 were seeded onto MATRIGEL™ coated 24-well dishes (1:30 dilution), and differentiated according to the methods described in Example 1 up to stage 5. Following this, the cells were grown for eight days in DMEM/F12+1% B27 and then treated for four days in DMEM/F12+1% B27 containing a cyclin dependent kinase inhibitor at a final concentration of 0.6125, 1.25, or 5.0 µM. We tested 6 inhibitors: PubChem ID#5330812 (EMD cat#217714), PubChem ID#4566 (EMD cat#217713), PubChem ID#5330797 (EMD cat#219476), PubChem ID#73292 (EMD cat#341251), PubChem ID#4592 (EMD cat#495620), and PubChem ID#160355 (EMD cat #557360). Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as the fold change relative to the vehicle treated control, as measured by real-time PCR.

We observed that the compounds PubChem ID#5330812, PubChem ID#4566, PubChem ID#5330797, and PubChem ID#73292 all stimulated MAFA expression at the concentrations tested (Table 4). PubChem ID#4592 and PubChem ID#160355 did not stimulate MAFA at the concentrations tested (Table 4). The compounds PubChem ID#5330812, PubChem ID#4566, PubChem ID#5330797, PubChem ID#4592 and PubChem ID#160355 all appeared to stimulate insulin expression (Table 4). The compound PubChem ID#5330797 reduced both glucagon and Arx4 expression (Table 4) while stimulating MAFA expression.

Example 9

Differentiation of Human Embryonic Stem Cells of the Cell Line H1 to Pancreatic Endocrine Cells with DMEM Containing 25 mM Glucose (DMEM-HG), Lacking Fetal Bovine Serum Cells of the human embryonic stem cells line H1 were cultured on MATRIGEL®-coated dishes (1:30 dilution) and differentiated into cells expressing markers characteristic of the pancreatic endocrine lineage using the following protocol:

a. RPMI medium supplemented with 2% BSA (Catalog#152401, MP Biomedical, Ohio), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, N.J.), for one day followed by treatment with RPMI media supplemented with 2% BSA and 100 ng/ml activin A plus 8 ng/ml of bFGF for an additional two days (Stage 1), then b. RPMI medium supplemented with 2% BSA+50 ng/ml FGF7+0.25 µM Cyclopamine-KAAD (#239804, Calbiochem, Calif.) for two days (Stage 2), then c. DMEM-HG+1% B27 (Invitrogen, Calif.)+50 ng/ml FGF7+0.25 µM Cyclopamine-KAAD+2 µM Retinoic acid (RA) (Sigma, Mo.)+100 ng/ml of Noggin (R & D Systems, Minn.) for six days (Stage 3), then d. DMEM-HG+1% B27 (Invitrogen, Calif.)+100 ng/ml Noggin+1 µM ALK5 inhibitor II (Catalog#616452, Calbiochem, Calif.) for three days (Stage 4), then e. DMEM-HG+1% B27 (Invitrogen, Calif.)+1 µM ALK5 inhibitor II (Calbiochem, Calif.) for seven days (Stage 5).

Medium was changed daily. At each stage the cell number was calculated using a hemocytometer and RNA was collected for PCR analysis. All samples were collected in triplicate.

Example 10

Screening of the Effects of Compounds from the EMD Kinase Inhibitor Library I on Cells Treated According to the Differentiation Protocol Outlined in Example 9

Cells of the human embryonic stem cell line H1 at passage 45 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, Calif.), 1 µM ALK5 inhibitor II (Calbiochem, Calif.) and a compound from an EMD Calbiochem compound library 1 solubilized in DMSO (Catalog#539744, Calbiochem, San Diego, Calif.) and treated at a final concentration of 2.5 µM. Wells containing vehicle were included as a control. Throughout the protocol media was changed daily except at stage 5 when media was changed every other day. All samples were treated in duplicate At the completion of this treatment RNA was collected for PCR analysis. Samples were analyzed by real-time PCR for expression of MAFA. Results are expressed as the fold increase in MAFA expression versus untreated H1 human embryonic stem cells (Table 5), as measured by real-time PCR Treatment of cells expressing markers characteristic of the pancreatic endocrine lineage with compounds A4 (Cat#, 124001, Akt Inhibitor IV), E8 (Cat#527450, PKR Inhibitor), and F9 (Cat#539648, Staurosporine, N-benzoyl-) at a 2.5 µM concentration resulted in an increase in MAFA expression at least 4 fold higher than vehicle treated controls (Table 5). Treatment with the compound E6 (Cat#521233, PDGF Receptor Tyrosine Kinase Inhibitor IV) at a 2.5 µM concentration resulted in an increase in MAFA expression at least 2.5 fold higher than vehicle treated controls (Table 5).

Example 11

Screening of the Effects of Compounds from the EMD Kinase Inhibitor Library II on Cells Treated According to the Differentiation Protocol Outlined in Example 9

Cells of the human embryonic stem cell line H1 at passage 46 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, Calif.), 1 µM ALK5 inhibitor II (Calbiochem, Calif.) (Stage 5) and a compound from an EMD Calbiochem compound library II solubilized in DMSO (Tables 1 and 6, Calbiochem, San Diego, Calif.) and treated at a final concentration of 2.5 µM. Wells containing vehicle were included as a control. Throughout the protocol media was changed daily except at stage 5 when media was changed every other day. All samples were treated in duplicate.

Figure 9:
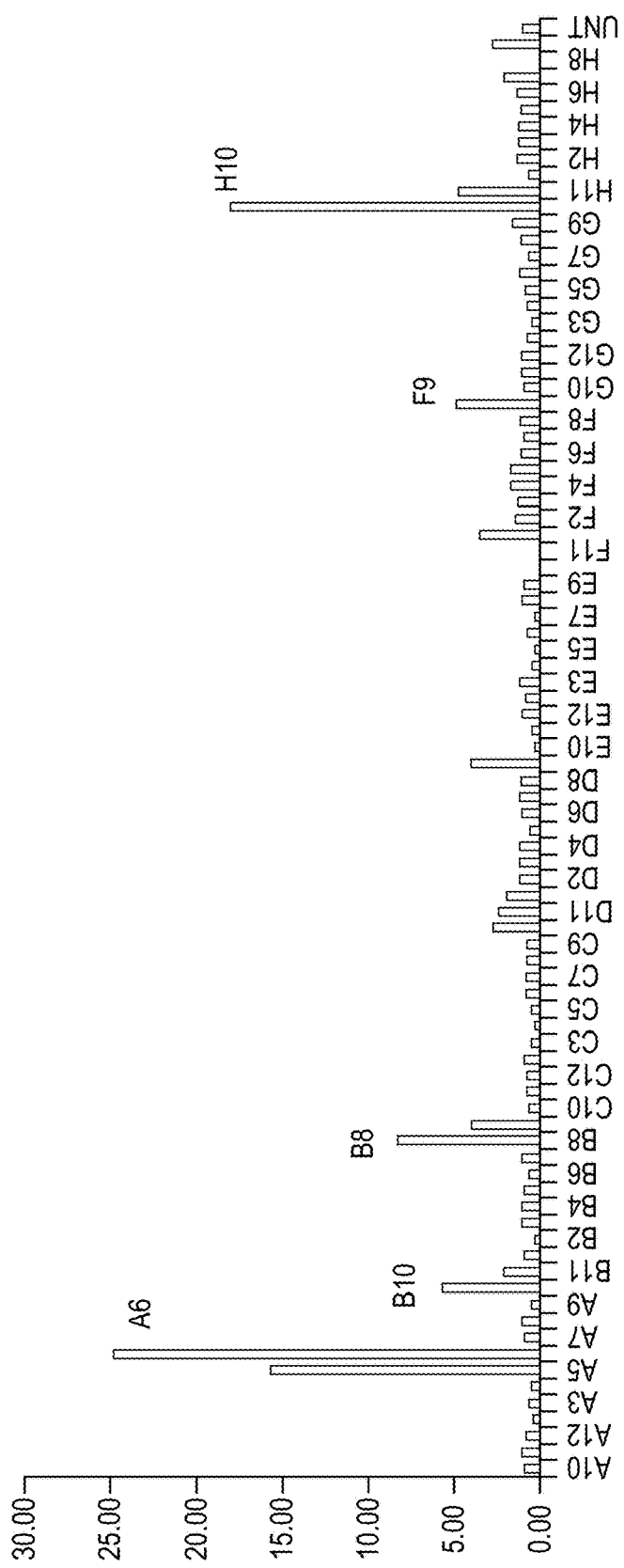
FIG. 9 shows the effect of compounds from the EMD Calbiochem kinase inhibitor library I on the expression of MAFA in cells expressing markers characteristic of the pancreatic endocrine lineage, as determined by real-time PCR.
Figure 10B:
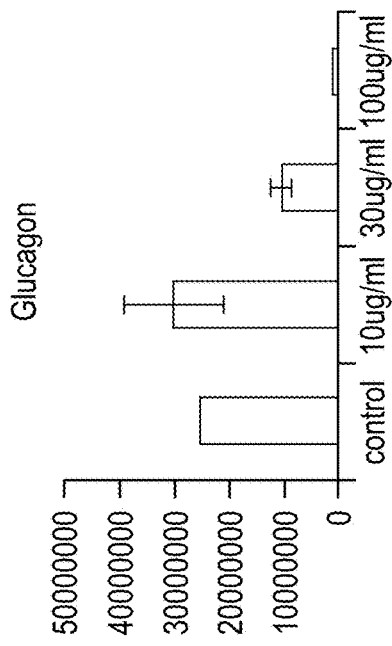
FIGS. 10A-D show the effect of genestein on the mRNA expression of insulin, glucagon, somatostatin and MAFA in cells expressing markers characteristic of the pancreatic endocrine lineage, as determined by real-time PCR.
Figure 10D:
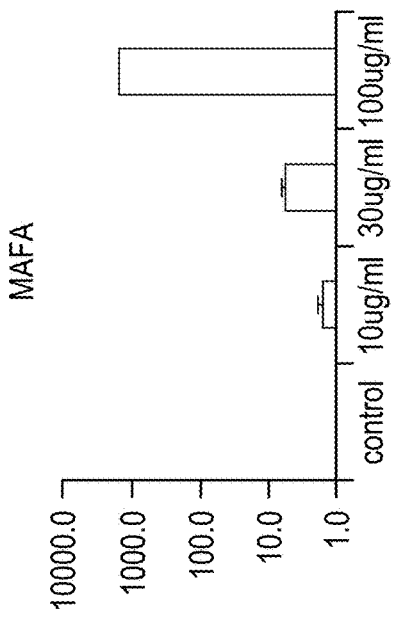
Figure 10A:
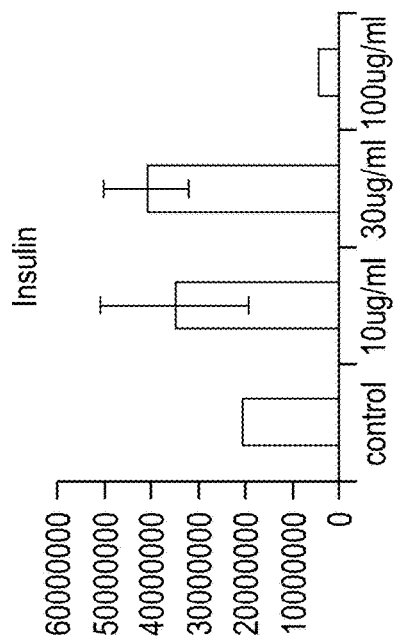
Figure 10C:
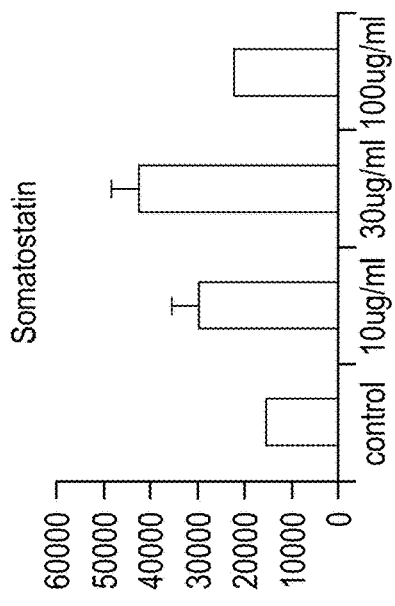

At the completion of this treatment RNA was collected for PCR analysis. Samples were analyzed by real-time PCR for expression of MAFA. Results for compounds that stimulated the expression of MAFA are shown and expressed as the fold increase in MAFA expression versus control samples (FIG. 9), as measured by real-time PCR.

Treatment of cells expressing markers characteristic of the pancreatic endocrine lineage with either: Alsterpaullone, 2-Cyanoethyl; SU9516; Alsterpaullone; Cdk1/2 Inhibitor III; Casein Kinase I Inhibitor, D4476; or MEK1/2 Inhibitor at a 2.5 µM concentration resulted in a 4.5 fold increase in MAFA expression versus untreated controls (Table 7).

Example 12

Inhibiting Cell Cycle Progression in Cells Expressing Markers Characteristic of the Pancreatic Endocrine Lineage with Small Molecule Inhibitors Promotes MAFA Expression in Cells Expressing Markers Characteristic of the Pancreatic Endocrine Lineage Cell growth resulting from cell cycle progression can be activated and maintained by stimulating cells with extracellular growth factors. Growth factors bind to the extracellular domains of growth factor receptors, inducing a conformational switch in the receptor's intracellular domain. This shift initiates receptor dimerization and activation of tyrosine kinases located on the intracellular domain of the receptor leading to phosphorylation and activation of multiple serine/threonine kinases downstream, ultimately resulting in cell cycle progression and cell proliferation.

Under normal physiologic conditions mature pancreatic beta cells, characterized by expression of insulin and the transcription factor MAFA, are quiescent and tend to remain in G0 of the cell cycle. Yet, in order to generate enough cells to form a functional organ and meet the needs of a mature animal, the cells expressing markers characteristic of the pancreatic endocrine lineage of the present invention must be cell cycling. Consequently, at some point in embryonic development, the cells expressing markers characteristic of the pancreatic endocrine lineage of the present invention differentiate to beta cells and transition from an actively cell-cycling proliferating cell, to a quiescent cell.

Our data indicate that by inhibiting cell cycle progression by blocking signaling cascades with small molecule kinase inhibitors, we can induce the cells expressing markers characteristic of the pancreatic endocrine lineage to express MAFA, a marker of mature pancreatic beta cells. Kinase inhibitors targeted to a growth factor receptor, (PDGF Receptor Tyrosine Kinase Inhibitor IV), or inhibitors which disrupt kinases downstream of tyrosine kinase receptors (MEK1/2 Inhibitor, PKR Inhibitor, or Akt Inhibitor IV) disrupt proliferative growth factor/kinase based signaling resulting in cell cycle arrest and induction of MAFA expression. Use of a broad spectrum inhibitor like staurosporine, can effectively induce MAFA, however it is also cytotoxic at effective concentrations. More directed compounds like cyclin dependent kinase inhibitors (Alsterpaullone, 2-Cyanoethyl; SU9516; Alsterpaullone; or Cdk1/2 Inhibitor III) induce MAFA with less toxicity than a broad spectrum inhibitor like staurosporine.

In order to determine if a broad spectrum kinase inhibitor could induce MAFA expression and a more mature phenotype in the cells expressing markers characteristic of the pancreatic endocrine lineage of the present invention we differentiated H1 human ES cells according to the methods described in example 9, and treated them on days 1, 3, and 5 of stage 5 with the protein-tyrosine kinase inhibitor, Genistein, which has been shown to induce G2 phase arrest in human and murine cell lines and inhibit multiple kinases. At doses of 10 and 30 ng/ml the endocrine hormones insulin, somatostatin, and the transcription factor MAFA, all showed increased expression versus untreated controls, while at 10 ng/ml the endocrine hormone glucagon had increased expression (FIGS. 10A-D). We observed significant toxicity at a 100 ng/ml dose of genistein that correlated with loss of insulin, glucagon, and somatostatin expression.

This data indicates that by inhibiting cell cycle progression by blocking signaling cascades with small molecule kinase inhibitors targeted to inhibit signal transduction from a growth factor receptor tyrosine kinase through intracellular signaling kinases to the nucleus and cyclin dependent kinases, we can induce the cells expressing markers characteristic of the pancreatic endocrine lineage of the present invention to express MAFA, a marker of mature pancreatic beta cells.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE 1

AlphaNumeric Well Label and the Corresponding PubChem ID# for EMDCalbiochem ® Kinase Inhibitor II compound library

| Well | PubChemID# | Well | PubChemID# | Well | PubChemID# | Well | PubChemID# |
|---|---|---|---|---|---|---|---|
| A2 | 16760529 | B2 | 16760303 | C2 | 5330797 | D2 | 9797929 |
| A3 | 5278396 | B3 | 5326739 | C3 | 3004085 | D3 | 11493598 |
| A4 | 6605258 | B4 | 5353431 | C4 | 481747 | D4 | 16760417 |
| A5 | 5005498 | B5 | 2422 | C5 | 1893668 | D5 | 73292 |
| A6 | 16760286 | B6 | 5472558 | C6 | 9969021 | D6 | 4124851 |
| A7 | 5326843 | B7 | 2794188 | C7 | 2856 | D7 | 6539732 |
| A8 | 3641059 | B8 | 5330812 | C8 | 6918386 | D8 | 448014 |
| A9 | 6604931 | B9 | 438981 | C9 | 10202471 | D9 | 5287844 |
| A10 | 11524144 | B10 | 6419753 | C10 | 9549301 | D10 | 6538818 |
| A11 | 9549303 | B11 | 16760346 | C11 | 5339183 | D11 | 10020713 |
| E2 | 5312137 | F2 | 11382492 | G2 | 6419739 | H2 | 176155 |
| E3 | 6419766 | F3 | 11624601 | G3 | 4665 | H3 | 16219471 |
| E4 | 6419741 | F4 | 490561 | G4 | 4713 | H4 | 3387354 |
| E5 | 3674 | F5 | 3820 | G5 | 4712 | H5 | 5174 |
| E6 | 9903786 | F6 | 5312122 | G6 | 5164 | H6 | 5228 |
| E7 | 6419764 | F7 | 9951490 | G7 | 4987 | H7 | 16760659 |
| E8 | 8515 | F8 | 389898 | G8 | 9549289 | H8 | 451705 |
| E9 | 11665831 | F9 | 9549284 | G9 | 5702541 | H9 | 16760660 |
| E10 | 11422035 | F10 | 11644425 | G10 | 5162 | H10 | 5289419 |
| E11 | 16760525 | F11 | 509554 | G11 | 5353940 | H11 | 9549300 |

TABLE 2

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage. The AlphaNumeric well# corresponds to the compound identity in Table 3.

| | Ratio vs. Control | |
|---|---|---|
| Well # | Insulin to Glucagon | MAFA to Arx4 |
| B1 | 1.6 | 0.9 |
| B2 | 2.4 | 1.3 |
| B3 | 2.9 | 2.9 |
| B4 | 1.1 | 2.0 |
| B5 | 1.3 | 1.3 |
| B6 | 1.6 | 16.3 |
| B7 | 1.3 | 0.5 |
| B8 | 1.6 | 0.5 |
| B9 | 1.1 | 1.5 |
| B10 | 1.2 | 1.5 |
| B11 | 1.1 | 2.1 |
| B12 | 1.0 | 2.0 |
| C1 | 0.7 | 0.8 |
| C2 | 0.9 | 1.0 |
| C3 | 1.3 | 0.9 |
| C4 | 1.2 | 1.7 |
| C5 | 1.0 | 1.1 |
| C6 | 1.6 | 1.2 |
| C7 | 4.3 | 0.2 |
| C8 | 40.2 | 84.3 |
| C9 | 0.8 | 0.5 |
| C10 | 2.3 | 1.9 |
| C11 | 1.1 | 0.4 |
| C12 | 1.0 | 0.4 |
| D1 | 2.7 | 1.2 |
| D2 | 3.4 | 1.3 |
| D3 | 1.7 | 2.1 |
| D4 | 5.8 | 6.4 |
| D5 | 1.4 | 1.1 |
| D6 | 1.8 | 3.9 |
| D7 | 1.7 | 0.6 |
| D8 | 2.8 | 5.1 |
| D9 | 1842.5 | 212.6 |
| D10 | 0.9 | 1.3 |
| D11 | 1.0 | 0.7 |
| D12 | 1.1 | 2.5 |
| E1 | 1.1 | 0.9 |
| E2 | 0.8 | 0.8 |
| E3 | 1.2 | 1.0 |
| E4 | 2.1 | 1.3 |
| E5 | 1.3 | 1.1 |
| E6 | 2.0 | 1.5 |
| E7 | 4.8 | 0.2 |
| E8 | 3.7 | 0.0 |
| E9 | 1.0 | 0.8 |
| E10 | 0.6 | 0.2 |
| E11 | 1.0 | 0.3 |
| E12 | 0.8 | 0.2 |
| F1 | 10.3 | 9.5 |
| F2 | 2.9 | 1.9 |
| F3 | 2.6 | 2.5 |
| F4 | 1.5 | 2.7 |
| F5 | 1.9 | 1.4 |
| F6 | 1.6 | 1.2 |
| F7 | 1.9 | 0.6 |
| F8 | 1.5 | 0.6 |
| F9 | 1.0 | 1.4 |
| F10 | 5.4 | 3.4 |
| F11 | 0.8 | 1.9 |
| F12 | 1.0 | 1.4 |
| G1 | 0.8 | 1.2 |
| G2 | 0.6 | 1.1 |
| G3 | 2.0 | 1.6 |
| G4 | 1.3 | 1.6 |
| G5 | 1.7 | 1.5 |
| G6 | 1.5 | 1.3 |
| G7 | 4.6 | 0.2 |
| G8 | 3.9 | 0.4 |
| G9 | 1.0 | 0.7 |
| G10 | 1.3 | 0.7 |
| G11 | 1.9 | 0.6 |
| G12 | 1.4 | 0.8 |
| H1 | 3.1 | 0.6 |
| H2 | 1.8 | 3.5 |
| H3 | 1.8 | 3.9 |
| H4 | 1.2 | 4.0 |

TABLE 2-continued

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage. The AlphaNumeric well# corresponds to the compound identity in Table 3.

| Well # | Ratio vs. Control | |
|---|---|---|
|  | Insulin to Glucagon | MAFA to Arx4 |
| H5 | 1.8 | 2.0 |
| H6 | 1.4 | 2.9 |
| H7 | 1.5 | 0.6 |
| H8 | 2.1 | 0.8 |
| vehicle control | 1.0 | 1.0 |

TABLE 3

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| B1 | EI-360 | 167869-21-8 | PD-98059 |
| B2 | EI-282 | 109511-58-2 | U-0126 |
| B3 | EI-286 | 152121-47-6 | SB-203580 |
| B4 | EI-148 | 84477-87-2 | H-7 |
| B5 | EI-195 | 84468-17-7 | H-9 |
| B6 | EI-156 | 62996-74-1 | Staurosporine |
| B7 | EI-228 | 133550-35-5 | AG-494 |
| B8 | EI-267 |  | AG-825 |
| B9 | EI-185 | 125697-92-9 | Lavendustin A |
| B10 | EI-253 | 136831-49-7 | RG-14620 |
| B11 | EI-191 | 118409-57-7 | Tyrphostin 23 |
| B12 | EI-187 | 118409-58-8 | Tyrphostin 25 |
| C1 | EI-257 | 122520-85-8 | Tyrphostin 46 |
| C2 | EI-188 | 122520-86-9 | Tyrphostin 47 |
| C3 | EI-189 | 122520-90-5 | Tyrphostin 51 |
| C4 | EI-190 | 2826-26-8 | Tyrphostin 1 |
| C5 | EI-335 | 116313-73-6 | Tyrphostin AG 1288 |
| C6 | EI-277 | 63177-57-1 | Tyrphostin AG 1478 |
| C7 | AC-1133 | 71897-07-9 | Tyrphostin AG 1295 |
| C8 | EI-215 | 10537-47-0 | Tyrphostin 9 |
| C9 | EI-247 |  | HNMPA (Hydroxy-2-naphthalenylmethylphosphonic acid) |
| C10 | EI-370 | 120685-11-2 | PKC-412 |
| C11 | EI-271 | 10083-24-6 | Piceatannol |
| C12 | EI-275 | 172889-26-8 | PP1 |
| D1 | EI-272 | 133550-35-3 | AG-490 |
| D2 | EI-263 |  | AG-126 |
| D3 | EI-229 |  | AG-370 |
| D4 | EI-258 |  | AG-879 |
| D5 | ST-420 | 154447-36-6 | LY 294002 |
| D6 | ST-415 | 19545-26-7 | Wortmannin |
| D7 | EI-246 | 133052-90-1 | GF 109203X |
| D8 | EI-226 | 548-04-9 | Hypericin |
| D9 | EI-283 | 138489-18-6 | Ro 31-8220 |
| D10 | EI-155 | 123-78-4 | Sphingosine |
| D11 | EI-196 | 127243-85-0 | H-89 |
| D12 | EI-158 | 84478-11-5 | H-8 |
| E1 | EI-184 | 91742-10-8 | HA-1004 |
| E2 | EI-233 | 103745-39-7 | HA-1077 |
| E3 | EI-232 |  | HDBA (2-Hydroxy-5-(2,5-dihydroxybenzylamino)benzoic acid) |
| E4 | EI-230 | 127191-97-3 | KN-62 |
| E5 | EI-268 |  | KN-93 |
| E6 | EI-197 | 109376-83-2 | ML-7 |
| E7 | EI-153 | 105637-50-1 | ML-9 |
| E8 | CC-100 | 452-06-2 | 2-Aminopurine |
| E9 | CC-202 | 158982-15-1 | N9-Isopropyl-olomoucine |
| E10 | CC-200 | 101622-51-9 | Olomoucine |
| E11 | CC-201 | 101622-50-8 | iso-Olomoucine |
| E12 | CC-205 | 186692-46-6 | Roscovitine |
| F1 | EI-293 | 24386-93-4 | 5-Iodotubercidin |
| F2 | EI-295 | 62004-35-7 | LFM-A13 |
| F3 | EI-294 | 152121-30-7 | SB-202190 |
| F4 | EI-297 | 172889-27-9 | PP2 |
| F5 | EI-298 | 208260-29-1 | ZM 336372 |

TABLE 3-continued

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| F6 | EI-306 | 5812-07-7 | SU 4312 |
| F7 | EI-303 | 146535-11-7 | AG-1296 |
| F8 | EI-307 | 220904-83-6 | GW 5074 |
| F9 | AC-1121 | 6865-14-1 | Palmitoyl-DL-carnitine Cl |
| F10 | EI-270 | 82-08-6 | Rottlerin |
| F11 | EI-147 | 446-72-0 | Genistein |
| F12 | ST-110 | 486-66-8 | Daidzein |
| G1 | EI-146 | 63177-57-1 | Erbstatin analog |
| G2 | AC-1142 | 6151-25-3 | Quercetin dihydrate |
| G3 | AC-1293 | | SU1498 |
| G4 | EI-357 | 4452-06-6 | ZM 449829 |
| G5 | EI-278 | 195462-67-7 | BAY 11-7082 |
| G6 | EI-231 | 53-85-0 | DRB (5,6-Dichloro-1-β-D-ribofuranosylbenzimidazole) |
| G7 | EI-273 | | HBDDE (2,2',3,3',4,4'-Hexahydroxy-1,1'-biphenyl-6,6'-dimethanol dimethyl ether) |
| G8 | EI-305 | 129-56-6 | SP 600125 |
| G9 | CC-206 | 479-41-4 | Indirubin |
| G10 | CC-207 | 160807-49-8 | Indirubin-3'-monoxime |
| G11 | EI-299 | 146986-50-7 | Y-27632 |
| G12 | EI-310 | 142273-20-9 | Kenpaullone |
| H1 | EI-328 | 121-40-4 | Terreic acid |
| H2 | EI-332 | 35943-35-2 | Triciribine |
| H3 | EI-336 | | BML-257 |
| H4 | EI-343 | | SC-514 |
| H5 | EI-344 | | BML-259 |
| H6 | EI-345 | 520-36-5 | Apigenin |
| H7 | EI-346 | | BML-265 (Erlotinib analog) |
| H8 | A-275 | 53123-88-9 | Rapamycin |

TABLE 4

The Effect of compounds of the BIOMOL Inhibitor compound library on the Expression of Insulin, glucagon, MAFA and Arx4 in Cells Expressing Markers Characteristic of the Pancreatic Endocrine Lineage

| Concentration and PubChem ID# | MAFA | Insulin | Glucagon | Arx4 |
|---|---|---|---|---|
| 0.61 μM 5330812 | 46.3 | 0.9 | 0.26 | 0.68 |
| 1.25 μM 5330812 | 209.2 | 1.3 | 0.31 | 0.66 |
| 5.0 μM 5330812 | 2909.9 | 66.3 | 4.71 | 0.92 |
| 0.61 μM 4566 | 1.0 | 1.0 | 0.77 | 0.78 |
| 1.25 μM 4566 | 0.8 | 1.1 | 0.90 | 0.78 |
| 5.0 μM 4566 | 1.0 | 1.1 | 0.96 | 0.69 |
| 0.61 μM 5330797 | 0.7 | 0.6 | 0.34 | 0.36 |
| 1.25 μM 5330797 | 1.5 | 0.8 | 0.25 | 0.37 |
| 5.0 μM 5330797 | 6.3 | 1.3 | 0.04 | 0.16 |
| 0.61 μM 73292 | 0.7 | 0.7 | 0.29 | 0.38 |
| 1.25 μM 73292 | 1.3 | 1.0 | 0.25 | 0.42 |
| 5.0 μM 73292 | 3.1 | 0.8 | 0.13 | 0.33 |
| 0.61 μM 4592 | 0.9 | 0.9 | 0.81 | 0.61 |
| 1.25 μM 4592 | 1.0 | 1.0 | 0.70 | 0.54 |
| 5.0 μM 4592 | 0.6 | 1.3 | 1.08 | 0.77 |
| 0.61 μM 160355 | 0.9 | 0.9 | 0.76 | 0.77 |
| 1.25 μM 160355 | 0.7 | 1.0 | 0.61 | 0.65 |
| 5.0 μM 160355 | 0.8 | 1.1 | 0.59 | 0.86 |
| Vehicle Treated | 1.0 | 1.0 | 1.00 | 1.00 |

TABLE 5

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| A10 | 197221 | Bcr-abl Inhibitor | 1.5 |
| A11 | 203290 | Bisindolylmaleimide I | 0.8 |
| A12 | DMSO | Control | 1.5 |
| A2 | 121767 | AG 1024 | 0.8 |
| A3 | 121790 | AGL 2043 | 0.8 |
| A4 | 124011 | Akt Inhibitor IV | 45.7 |
| A5 | 124012 | Akt Inhibitor V, Triciribine | 0.9 |
| A6 | 124018 | Akt Inhibitor VIII, Isozyme-Selective, Akti-1/2 | 1.6 |
| A7 | 124020 | Akt Inhibitor X | 1.4 |
| A8 | 521275 | PDK1/Akt/Flt Dual Pathway Inhibitor | 2.1 |
| A9 | 189404 | Aurora Kinase Inhibitor II | 1.3 |
| B10 | 317200 | DMBI | 1.9 |
| B11 | 324673 | EGFR/ErbB-2 Inhibitor | 2.4 |
| B12 | DMSO | Control | 1.9 |
| B2 | 203297 | Bisindolylmaleimide IV | 1.9 |
| B3 | 203696 | BPIQ-I | 1.6 |
| B4 | 220285 | Chelerythrine Chloride | 2.3 |
| B5 | 234505 | Compound 56 | 1.8 |
| B6 | 260961 | DNA-PK Inhibitor II | 2.0 |
| B7 | 260962 | DNA-PK Inhibitor III | 2.2 |
| B8 | 528100 | PI-103 | 1.9 |
| B9 | 266788 | Diacylglycerol Kinase Inhibitor II | 1.5 |
| C10 | 375670 | Herbimycin A, *Streptomyces* sp. | 1.3 |
| C11 | 343022 | Flt-3 Inhibitor III | 1.1 |
| C12 | DMSO | Control | 1.1 |
| C2 | 324674 | EGFR Inhibitor | 3.5 |
| C3 | 324840 | EGFR/ErbB-2/ErbB-4 Inhibitor | 0.9 |
| C4 | 343020 | Flt-3 Inhibitor | 0.6 |

TABLE 5-continued

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| C5 | 343021 | Flt-3 Inhibitor II | 0.5 |
| C6 | 344036 | cFMS Receptor Tyrosine Kinase Inhibitor | 2.2 |
| C7 | 365250 | Gö 6976 | 1.9 |
| C8 | 365251 | Gö 6983 | 1.0 |
| C9 | 371806 | GTP-14564 | 0.7 |
| D10 | 440203 | LY 303511 | 1.7 |
| D11 | 448101 | Met Kinase Inhibitor | 2.1 |
| D12 | BLANK | | 1.7 |
| D2 | 407248 | IGF-1R Inhibitor II | 1.6 |
| D3 | 407601 | IRAK-1/4 Inhibitor | 2.2 |
| D4 | 420099 | JAK Inhibitor I | 1.4 |
| D5 | 420104 | JAK3 Inhibitor II | 2.0 |
| D6 | 420121 | JAK3 Inhibitor IV | 1.7 |
| D7 | 420126 | JAK3 Inhibitor VI | 1.9 |
| D8 | 428205 | Lck Inhibitor | 1.9 |
| D9 | 440202 | LY 294002 | 2.3 |
| E10 | 528106 | PI 3-Kg Inhibitor | 1.6 |
| E11 | 528108 | PI 3-KbInhibitor II | 1.4 |
| E12 | BLANK | | 1.6 |
| E2 | 513035 | PD 158780 | 0.8 |
| E3 | 513040 | PD 174265 | 1.0 |
| E4 | 521231 | PDGF Receptor Tyrosine Kinase Inhibitor II | 0.8 |
| E5 | 521232 | PDGF Receptor Tyrosine Kinase Inhibitor III | 1.7 |
| E6 | 521233 | PDGF Receptor Tyrosine Kinase Inhibitor IV | 5.5 |
| E7 | 521234 | PDGF RTK Inhibitor | 1.9 |
| E8 | 527450 | PKR Inhibitor | 24.6 |
| E9 | 527455 | PKR Inhibitor, Negative Control | 1.5 |
| F10 | 567805 | Src Kinase Inhibitor I | 2.3 |
| F11 | 572660 | SU11652 | 1.7 |
| F12 | DMSO | Control | 2.1 |
| F2 | 529574 | PP3 | 1.3 |
| F3 | 529581 | PP1 Analog II, 1NM-PP1 | 2.3 |
| F4 | 539652 | PKCbII/EGFR Inhibitor | 1.8 |
| F5 | 539654 | PKCb Inhibitor | 1.6 |
| F6 | 553210 | Rapamycin | 1.2 |
| F7 | 555553 | Rho Kinase Inhibitor III, Rockout | 1.7 |
| F8 | 555554 | Rho Kinase Inhibitor IV | 2.3 |
| F9 | 539648 | Staurosporine, N-benzoyl- | 11.7 |
| G10 | 658550 | AG 1295 | 1.4 |
| G11 | 658551 | AG 1296 | 1.1 |
| G12 | DMSO | Control | 1.2 |
| G2 | 574711 | Syk Inhibitor | 1.2 |
| G3 | 574712 | Syk Inhibitor II | 0.8 |
| G4 | 574713 | Syk Inhibitor III | 1.1 |
| G5 | 616451 | TGF-b RI Kinase Inhibitor | 1.1 |
| G6 | 616453 | TGF-b RI Inhibitor III | 1.6 |
| G7 | 658390 | AG 9 | 1.5 |
| G8 | 658401 | AG 490 | 1.4 |
| G9 | 658440 | AG 112 | 1.4 |
| H10 | 189405 | Aurora Kinase Inhibitor III | 2.0 |
| H11 | 569397 | Staurosporine, *Streptomyces* sp. | 0.0* |
| H12 | DMSO | Control | 1.5 |
| H2 | 658552 | AG 1478 | 2.7 |
| H3 | 676480 | VEGF Receptor 2 Kinase Inhibitor I | 1.7 |
| H4 | 676481 | VEGF Receptor Tyrosine Kinase Inhibitor II | 1.0 |
| H5 | 676482 | VEGF Receptor Tyrosine Kinase Inhibitor III, KRN633 | 1.6 |
| H6 | 676485 | VEGF Receptor 2 Kinase Inhibitor II | 1.0 |
| H7 | 676487 | VEGF Receptor 2 Kinase Inhibitor III | 1.1 |
| H8 | 676489 | VEGF Receptor 2 Kinase Inhibitor IV | 2.1 |
| H9 | 260964 | DNA-PK Inhibitor V | 1.5 |

TABLE 6

AlphaNumeric Well Label, Corresponding Catalog#, and Compound # for EMD Calbiochem ® Kinase Inhibitor II compound library

| Well # | Catalog # | Compound # |
|---|---|---|
| A1 | DMSO | |
| A2 | 422706 | KN-62 |
| A3 | 118500 | ATM Kinase Inhibitor |
| A4 | 118501 | ATM/ATR Kinase Inhibitor |
| A5 | 126870 | Alsterpaullone |
| A6 | 126871 | Alsterpaullone, 2-Cyanoethyl |
| A7 | 128125 | Aloisine A, RP107 |
| A8 | 128135 | Aloisine, RP106 |
| A9 | 164640 | Aminopurvalanol A |
| A10 | 171260 | AMPK Inhibitor, Compound C |
| A11 | 189405 | Aurora Kinase Inhibitor III |
| A12 | BLANK | |
| B1 | DMSO | |
| B2 | 189406 | Aurora Kinase/Cdk Inhibitor |
| B3 | 402085 | Indirubin-3′-monoxime |
| B4 | 196870 | BAY 11-7082 |
| B5 | 203600 | Bohemine |
| B6 | 217695 | Cdk1 Inhibitor |
| B7 | 217696 | Cdk1 Inhibitor, CGP74514A |
| B8 | 217714 | Cdk1/2 Inhibitor III |
| B9 | 217720 | Cdk1/5 Inhibitor |
| B10 | 218696 | Casein Kinase I Inhibitor, D4476 |
| B11 | 218710 | Casein Kinase II Inhibitor III, TBCA |
| B12 | BLANK | |
| C1 | DMSO | |
| C2 | 219476 | Cdk4 Inhibitor |
| C3 | 219477 | Cdk4 Inhibitor II, NSC 625987 |
| C4 | 219478 | Cdk4 Inhibitor III |
| C5 | 219479 | Cdc2-Like Kinase Inhibitor, TG003 |
| C6 | 220486 | Chk2 Inhibitor II |
| C7 | 234503 | Compound 52 |
| C8 | 238803 | Cdk2 Inhibitor III |
| C9 | 238804 | Cdk2 Inhibitor IV, NU6140 |
| C10 | 219491 | Cdk/Crk Inhibitor |
| C11 | 328009 | ERK Inhibitor III |
| C12 | BLANK | |
| D1 | DMSO | |
| D2 | 688000 | ROCK Inhibitor, Y-27632 |
| D3 | 328007 | ERK Inhibitor II, FR180204 |
| D4 | 328008 | ERK Inhibitor II, Negative control |
| D5 | 341251 | Fascaplysin, Synthetic |
| D6 | 361540 | GSK-3b Inhibitor I |
| D7 | 361541 | GSK-3b Inhibitor II |
| D8 | 361549 | GSK-3b Inhibitor VIII |
| D9 | 361550 | GSK-3 Inhibitor IX |
| D10 | 361551 | GSK-3 Inhibitor X |
| D11 | 361553 | GSK-3b Inhibitor XI |
| D12 | BLANK | |
| E1 | DMSO | |
| E2 | 572635 | SU6656 |
| E3 | 361555 | GSK-3 Inhibitor XIII |
| E4 | 371957 | Isogranulatimide |
| E5 | 400090 | IC261 |
| E6 | 401481 | IKK-2 Inhibitor IV |
| E7 | 402081 | Indirubin Derivative E804 |
| E8 | 420119 | JNK Inhibitor II |
| E9 | 420123 | JNK Inhibitor, Negative Control |
| E10 | 420129 | JNK Inhibitor V |
| E11 | 420136 | JNK Inhibitor IX |
| E12 | BLANK | |
| F1 | DMSO | |
| F2 | 475863 | MK2a Inhibitor |
| F3 | 420135 | JNK Inhibitor VIII |
| F4 | 420298 | K-252a, *Nocardiopsis* sp. |
| F5 | 422000 | Kenpaullone |
| F6 | 422708 | KN-93 |
| F7 | 444937 | MEK Inhibitor I |
| F8 | 444938 | MEK Inhibitor II |
| F9 | 444939 | MEK1/2 Inhibitor |
| F10 | 454861 | MNK1 Inhibitor |
| F11 | 481406 | NF-κB Activation Inhibitor |
| F12 | BLANK | |
| G1 | DMSO | |
| G2 | 506121 | p38 MAP Kinase Inhibitor III |
| G3 | 506126 | p38 MAP Kinase Inhibitor |

TABLE 6-continued

AlphaNumeric Well Label, Corresponding Catalog#, and Compound # for EMD Calbiochem ® Kinase Inhibitor II compound library

| Well # | Catalog # | Compound # |
|---|---|---|
| G4 | 513000 | PD 98059 |
| G5 | 513030 | PD 169316 |
| G6 | 559396 | SB220025 |
| G7 | 540500 | Purvalanol A |
| G8 | 361554 | GSK3b Inhibitor XII, TWS119 |
| G9 | 371963 | H-89, Dihydrochloride |
| G10 | 559387 | SB 202474, Negative control for p38 MAPK inhibition studies |
| G11 | 559388 | SB 202190 |
| G12 | BLANK | |
| H1 | DMSO | |
| H2 | 559389 | SB 203580 |
| H3 | 371970 | HA 1077, Dihydrochloride Fasudil |
| H4 | 559402 | SB 218078 |
| H5 | 565625 | SC-68376 |
| H6 | 567305 | SKF-86002 |
| H7 | 567731 | Sphingosine Kinase Inhibitor |
| H8 | 569397 | Staurosporine, *Streptomyces* sp. |
| H9 | 570250 | STO-609 |
| H10 | 572650 | SU9516 |
| H11 | 616373 | Tpl2 Kinase Inhibitor |
| H12 | BLANK | |

TABLE 7

Fold Induction of MAFA expression by several Compounds from the EMD Kinase Inhibitor Library II on Cells Treated according to the Differentiation Protocol Outlined in Example 9

| well# | fold vs. control | cat# | drug name |
|---|---|---|---|
| A6 | 24.8 | 126871 | Alsterpaullone, 2-Cyanoethyl |
| H10 | 18.0 | 572650 | SU9516 |
| A5 | 15.3 | 126870 | Alsterpaullone |
| B8 | 8.2 | 217714 | Cdk1/2 Inhibitor III |
| B10 | 5.7 | 218696 | Casein Kinase I Inhibitor, D4476 |
| F9 | 4.92 | 444939 | MEK1/2 Inhibitor |

What is claimed is:

1. A method for increasing the expression of MAF bZIP transcription factor A ("MAFA") in cells expressing markers characteristic of the pancreatic endocrine lineage, the method comprising the steps of:
    a. sequentially differentiating human pluripotent stem cells to obtain cells expressing markers characteristic of the pancreatic endocrine lineage, wherein the cells expressing markers characteristic of the pancreatic endocrine lineage express PDX1; and
    b. culturing the cells expressing markers characteristic of the pancreatic endocrine lineage in medium comprising an added amount of a kinase inhibitor to cause an increase in expression of MAFA as compared to cells expressing markers characteristic of the pancreatic endocrine lineage that are not cultured in medium comprising the added kinase inhibitor, wherein the kinase inhibitor is i) cyclin-dependent kinase inhibitor, wherein the cyclin-dependent kinase inhibitor is a cyclin-dependent kinase 1, cyclin-dependent kinase 2, and/or a cyclin-dependent kinase 4 inhibitor or ii) an aurora kinase inhibitor, wherein the aurora kinase inhibitor is aurora kinase inhibitor II or aurora kinase inhibitor III.

2. The method of claim 1, wherein the cyclin-dependent kinase inhibitor is:
    ethyl-(6-hydroxy-4-phenylbenzo[4,5]furo[2,3-b])pyridine-3-carboxylate;
    6-cyclohexylmethoxy-2-(4'-sulfamoylanilino)purine;
    5-amino-34(4-(aminosulfonyl)phenyl)amino)-N-(2,6-difluorphenyl)-1h-1,2,4-triazole-1-carbothioamide; or
    2-bromo-12,13-dihydro-5H-indolo[2,3-a]pyrrolo[3,4-c]carbazole-5,7(6H)-dione.

3. The method of claim 1, wherein the cyclin-dependent kinase inhibitor is added to cells expressing markers characteristic of the pancreatic endocrine lineage at a concentration from about 0.1 µM to about 10 µM for about one to seven days.

4. The method of claim 1, wherein the cells expressing markers characteristic of the pancreatic endocrine lineage are pancreatic endocrine cells.

5. The method of claim 1, wherein the cyclin-dependent kinase inhibitor is 2-bromo-12,13-dihydro-5H-indolo[2,3-a]pyrrolo[3,4-c]carbazole-5,7(6H)-dione.

6. The method of claim 1, wherein the cyclin-dependent kinase inhibitor is ethyl-(6-hydroxy-4-phenylbenzo[4,5]furo[2,3-b])pyridine-3-carboxylate.

7. The method of claim 1, wherein the cyclin-dependent kinase inhibitor is 5-amino-3-((4-(amino sulfonyl)phenyl)amino)-N-(2,6-difluorphenyl)-1h-1,2,4-triazole-1-carbothioamide.

8. The method of claim 1, wherein the cyclin-dependent kinase inhibitor is 6-cyclohexylmethoxy-2-(4'-sulfamoylanilino)purine.

9. The method of claim 1, wherein the human pluripotent stem cells are human embryonic cells.

10. The method of claim 1, wherein the kinase inhibitor is the cyclin-dependent kinase inhibitor.

11. The method of claim 1, wherein the kinase inhibitor is the aurora kinase inhibitor.

12. The method of claim 11, wherein the aurora kinase inhibitor is aurora kinase inhibitor II.

13. The method of claim 11, wherein the aurora kinase inhibitor is aurora kinase inhibitor III.

* * * * *